(12) United States Patent
Anderson et al.

(10) Patent No.: US 9,974,595 B2
(45) Date of Patent: *May 22, 2018

(54) SYSTEMS AND METHODS FOR OPTIMIZING EMISSIONS FROM SIMULTANEOUS ACTIVATION OF ELECTROSURGERY GENERATORS

(71) Applicant: COVIDIEN LP, Mansfield, MA (US)

(72) Inventors: Randall L. Anderson, Longmont, CO (US); Donald W. Heckel, Thornton, CO (US)

(73) Assignee: COVIDIEN LP, Mansfield, MA (US)

( * ) Notice: Subject to any disclaimer, the term of this patent is extended or adjusted under 35 U.S.C. 154(b) by 584 days.

This patent is subject to a terminal disclaimer.

(21) Appl. No.: 14/592,026

(22) Filed: Jan. 8, 2015

(65) Prior Publication Data

US 2015/0282860 A1    Oct. 8, 2015

Related U.S. Application Data

(60) Provisional application No. 61/975,101, filed on Apr. 4, 2014, provisional application No. 61/975,120, filed
(Continued)

(51) Int. Cl.
*A61B 18/12* (2006.01)
*A61B 18/18* (2006.01)
*A61B 18/00* (2006.01)

(52) U.S. Cl.
CPC .......... *A61B 18/1206* (2013.01); *A61B 18/18* (2013.01); *A61B 2018/0072* (2013.01);
(Continued)

(58) Field of Classification Search
CPC ............ A61B 18/18; A61B 2018/0072; A61B 2018/00732; A61B 2018/007567; A61B 2018/00869; A61B 2018/1273
See application file for complete search history.

(56) References Cited

U.S. PATENT DOCUMENTS 4,860,752 A    8/1989    Turner
6,283,974 B1   9/2001    Alexander
(Continued)

FOREIGN PATENT DOCUMENTS

DE    179607 C    3/1905
DE    390937 C    3/1924
(Continued)

OTHER PUBLICATIONS

Extended European Search Report for EP 15 15 9879 dated Oct. 5, 2015.
(Continued)

*Primary Examiner* — Catherine Voorhees

(57) ABSTRACT

A modular electrosurgical generator platform is presented including a power supply module configured to output power, a first energy module configured to receive the power and convert the power into a first waveform having a first phase, and to deliver the power in a first energy mode, and a second energy module configured to receive the power and convert the power into a second waveform having a second phase, and to deliver the power in a second energy mode. The modular electrosurgical generator platform also includes a host controller module to control a type and a number of energy modalities, a comparator for comparing the first phase of the first waveform with the second phase of the second waveform in one or more of a plurality of sub-periods and an adjustment module for adjusting a relative phase between the first and second waveforms based on results obtained from the comparator.

13 Claims, 20 Drawing Sheets

Related U.S. Application Data on Apr. 4, 2014, provisional application No. 61/975,126, filed on Apr. 4, 2014.

(52) U.S. Cl.
CPC ........... A61B 2018/0075 (2013.01); A61B 2018/00732 (2013.01); A61B 2018/00767 (2013.01); A61B 2018/00869 (2013.01); A61B 2018/1273 (2013.01)

(56) References Cited

U.S. PATENT DOCUMENTS

| | | | |
|---|---|---|---|
| 6,944,504 B1 * | 9/2005 | Arndt | A61B 18/18 607/101 |
| 7,033,845 B2 | 4/2006 | Anderson et al. | |
| 8,394,092 B2 | 3/2013 | Brannan | |
| 8,636,664 B2 | 1/2014 | Brannan | |
| 2006/0284682 A1 * | 12/2006 | Lee | H03F 1/301 330/291 |
| 2007/0288079 A1 | 12/2007 | van der Weide et al. | |
| 2008/0125772 A1 * | 5/2008 | Stone | A61B 18/1492 606/41 |
| 2008/0147056 A1 | 6/2008 | van der Weide et al. | |
| 2009/0318916 A1 | 12/2009 | Lischinsky et al. | |
| 2010/0022999 A1 | 1/2010 | Gollnick et al. | |
| 2010/0030210 A1 * | 2/2010 | Paulus | A61B 18/1206 606/38 |
| 2011/0160717 A1 | 6/2011 | van der Weide et al. | |
| 2011/0306960 A1 * | 12/2011 | Eisele | A61B 18/1206 606/33 |
| 2012/0053577 A1 | 3/2012 | Lee et al. | |
| 2012/0277818 A1 | 11/2012 | Stancer et al. | |
| 2012/0310232 A1 | 12/2012 | Erez | |
| 2013/0023870 A1 | 1/2013 | Collins | |
| 2013/0023871 A1 * | 1/2013 | Collins | A61B 18/1233 606/34 |
| 2013/0035679 A1 * | 2/2013 | Orszulak | A61B 18/1445 606/33 |
| 2013/0304049 A1 * | 11/2013 | Behnke, II | A61B 18/1206 606/33 |
| 2015/0282857 A1 * | 10/2015 | Anderson | A61B 18/00 606/41 |
| 2015/0282861 A1 * | 10/2015 | Anderson | A61B 18/1206 606/37 |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 102005007769 A1 | 8/2006 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | S6196905 U | 6/1986 |
| JP | 63 005876 A | 1/1988 |
| JP | 2002-065690 A | 3/2002 |
| JP | 2005-185657 A | 7/2005 |
| SU | 166452 | 11/1964 |
| SU | 727201 A2 | 4/1980 |
| WO | 95/25472 A1 | 9/1995 |
| WO | 02/11634 A1 | 2/2002 |
| WO | 02/45589 A2 | 6/2002 |
| WO | 03/090635 A1 | 11/2003 |
| WO | 06/050888 A1 | 5/2006 |
| WO | 2007/099460 A2 | 9/2007 |
| WO | WO 2007099460 A2 * | 9/2007 ......... A61B 18/1206 |
| WO | 08/053532 A1 | 5/2008 |
| WO | 2011/129893 A1 | 10/2011 |

OTHER PUBLICATIONS

Wald et al., "Accidental Burns", JAMA, Aug. 16, 1971, vol. 217, No. 7, pp. 916-921.

Vallfors et al., "Automatically Controlled Bipolar Electrosoagulation-'COA-COMP'", Neurosurgical Review 7:2-3 (1984) pp. 187-190.

Sugita et al., "Bipolar Coagulator with Automatic Thermocontrol", J. Neurosurg., vol. 41, Dec. 1944, pp. 777-779.

Prutchi et al. "Design and Development of Medical Electronic Instrumentation", John Wiley & Sons, Inc. 2005.

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.

Muller et al. "Extended Left Hemicolectomy Using the LigaSure Vessel Sealing System", Innovations That Work; Company Newsletter; Sep. 1999.

"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.

Ogden Goertzel Alternative to the Fourier Transform: Jun. 1993 pp. 485-487, Electronics World; Reed Business Publishing, Sutton, Surrey, BG vol. 99, No. 9. 1687.

Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator", 3 pp. Jan. 1989.

(56) References Cited

OTHER PUBLICATIONS

Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690, filed Apr. 3, 2003 inventor: Behnke.
U.S. Appl. No. 10/573,713, filed Mar. 28, 2006 inventor: Wham.
U.S. Appl. No. 10/761,524, filed Jan. 21, 2004 inventor: Wham.
U.S. Appl. No. 11/242,458, filed Oct. 3, 2005 inventor: Becker.
U.S. Appl. No. 14/096,341, filed Dec. 4, 2013 inventor: Johnson.
U.S. Appl. No. 14/098,859, filed Dec. 6, 2013 inventor: Johnson.
U.S. Appl. No. 14/100,113, filed Dec. 9, 2013 inventor: Gilbert.
U.S. Appl. No. 14/147,294, filed Jan. 3, 2014 inventor: Gilbert.
U.S. Appl. No. 14/147,312, filed Jan. 3, 2014 inventor: Gilbert.
U.S. Appl. No. 14/168,296, filed Jan. 30, 2014, inventor: Mattmiller.
U.S. Appl. No. 14/174,551, filed Feb. 6, 2014 inventor: Johnson.
U.S. Appl. No. 14/174,607, filed Feb. 6, 2014 inventor: Friedrichs.
U.S. Appl. No. 14/179,724, filed Feb. 13, 2014 inventor: Johnson.
U.S. Appl. No. 14/180,965, filed Feb. 14, 2014 inventor: Larson.
U.S. Appl. No. 14/181,114, filed Feb. 14, 2014 inventor: Larson.
U.S. Appl. No. 14/182,797, filed Feb. 18, 2014 inventor: Wham.
U.S. Appl. No. 14/190,830, filed Feb. 26, 2014 inventor: Johnson.
U.S. Appl. No. 14/190,895, filed Feb. 26, 2014 inventor: Gilbert.
U.S. Appl. No. 14/255,051, filed Apr. 17, 2014 inventor: Coulson.
U.S. Appl. No. 14/262,219, filed Apr. 25, 2014 inventor: Gilbert.
U.S. Appl. No. 14/267,066, filed May 1, 2014, inventor: Friedrichs.
U.S. Appl. No. 14/268,187, filed May 2, 2014, inventor: Kerr.
U.S. Appl. No. 14/283,604, filed May 21, 2014, inventor: Behnke.
U.S. Appl. No. 14/297,771, filed Jun. 6, 2014, inventor: Wham.
U.S. Appl. No. 14/297,812, filed Jun. 6, 2014, inventor: Wham.
U.S. Appl. No. 14/297,890, filed Jun. 6, 2014, inventor: Wham.
U.S. Appl. No. 14/320,762, filed Jul. 1, 2014, inventor: Gilbert.
U.S. Appl. No. 14/320,804, filed Jul. 1, 2014, inventor: Gilbert.
Australian Examination Report No. 1 for AU 2015200376 dated Jan. 21, 2016.

* cited by examiner

Channel 1

Channel 2 out of phase (time lagged by 180°) with Channel 1

SYSTEMS AND METHODS FOR OPTIMIZING EMISSIONS FROM SIMULTANEOUS ACTIVATION OF ELECTROSURGERY GENERATORS

CROSS-REFERENCE TO RELATED APPLICATIONS

This application claims priority to, and the benefit of, U.S. Provisional Patent Application Ser. Nos. 61/975,101, 61/975,120, and 61/975,126, all of which were filed Apr. 4, 2014. This application is related to U.S. patent application Ser. Nos. 14/592,001 and 14/592,046, each of which were filed on Jan. 8, 2015. The entire contents of each of the above applications are hereby incorporated herein by reference.

BACKGROUND

1. Technical Field

The present disclosure relates to systems and methods for optimizing emissions from simultaneous activation of electrosurgery generators.

2. Background of Related Art

Electrosurgical generators are employed by surgeons in conjunction with an electrosurgical instrument to cut, coagulate, desiccate and/or seal patient tissue. High frequency electrical energy, e.g., radio frequency (RF) energy, is produced by the electrosurgical generator and applied to the tissue by an electrosurgical tool. Both monopolar and bipolar configurations are commonly used during electrosurgical procedures.

The electrical energy usually has its waveform shaped to enhance its ability to cut, coagulate or seal tissue. Different waveforms correspond to different modes of operation of the generator, and each mode gives the surgeon various operating advantages. Modes may include, but are not limited to, cut, coagulate, blend, desiccate, or spray. A surgeon may easily select and change the different modes of operation as the surgical procedure progresses.

In each mode of operation, the electrosurgical power delivered to the patient is regulated to achieve suitable surgical effect. Applying more electrosurgical power than necessary results in tissue destruction and prolongs healing. Applying less than the suitable amount of electrosurgical power inhibits the surgical procedure.

Electrosurgical techniques and instruments can be used to coagulate small diameter blood vessels or to seal large diameter vessels or tissue, e.g., veins and/or soft tissue structures, such as lung, and intestine. A surgeon can cauterize, coagulate/desiccate and/or simply reduce or slow bleeding, by controlling the intensity, frequency and duration of the electrosurgical energy applied between the electrodes and through the tissue. For the purposes herein, the term "cauterization" is defined as the use of heat to destroy tissue (also called "diathermy" or "electro-diathermy"). The term "coagulation" is defined as a process of desiccating tissue wherein the tissue cells are ruptured and dried.

"Vessel sealing" or "tissue fusion" is defined as the process of liquefying the collagen and elastin in the tissue so that it reforms into a fused mass with significantly-reduced demarcation between the opposing tissue structures (opposing walls of the lumen). Coagulation of small vessels is usually sufficient to permanently close them while larger vessels or tissue need to be sealed to assure permanent closure. It has been known that different waveforms of electrosurgical energy are suited for different surgical affects, e.g., cutting, coagulation, sealing, blend, etc. For example, the "cutting" mode typically entails generating a continuous sinusoidal waveform in the frequency range of 250 kHz to 4 MHz with a crest factor in the range of 1.4 to 2.0. The "blend" mode typically entails generating a periodic burst waveform with a duty cycle in the range of 25% to 75% and a crest factor in the range of 2.0 to 5.0. The "coagulate" mode typically entails generating a periodic burst waveform with a duty cycle of approximately 10% or less and a crest factor in the range of 5.0 to 12.0.

In order to optimize sealing or tissue fusion without causing unwanted charring of tissue at the surgical site or possibly causing collateral damage to adjacent tissue, e.g., thermal spread, it is necessary to accurately control the output from the electrosurgical generator, e.g., power, waveform, voltage, current, pulse rate, etc. It follows that accurate measurement of the output power of an electrosurgical generator greatly benefits the design, manufacture, and use thereof. Thus, there is continual need to improve delivery of energy to the tissue.

SUMMARY

In accordance with aspects of the present disclosure, a method of performing an electrosurgical procedure is presented. The method includes the steps of delivering first energy to a first target tissue via a first generator, the first energy represented as a first waveform having a first phase, delivering second energy to a second target tissue via a second generator, the second energy represented as a second waveform having a second phase, applying the first energy in a first energy mode in a predetermined time period, and applying the second energy in a second energy mode in the predetermined time period. The method also includes the steps of comparing the first phase of the first energy waveform with the second phase of the second energy waveform in one or more of the plurality of sub-periods, and adjusting a relative phase between the first and second energy waveforms based on the comparison step.

According to an aspect of the present disclosure, the adjusting step involves offsetting the first phase from the second phase by a predetermined amount.

According to a further aspect of the present disclosure, the offsetting results in destructive interference of the first and second energy waveforms. Alternatively, the offsetting involves constructive interference of the first and second energy waveforms.

According to a further aspect of the present disclosure, the first generator is coupled to a first micro-catheter and the second generator is coupled to a second micro-catheter. The first micro-catheter applies the first energy to the first target tissue and the second micro-catheter applies the second energy to the second target tissue.

According to another aspect of the present disclosure, a modular electrosurgical generator platform is presented. The modular electrosurgical generator platform includes a power supply module configured to output power; a first energy module configured to receive the power and convert the power into a first waveform having a first phase, and to deliver the power in a first energy mode; a second energy module configured to receive the power and convert the power into a second waveform having a second phase, and to deliver the power in a second energy mode; a host controller module configured to control a type and a number of energy modalities provided by the generator platform; a comparator for comparing the first phase of the first waveform with the second phase of the second waveform in one or more of a plurality of sub-periods; and an adjustment module for adjusting a relative phase between the first and second waveforms based on results obtained from the comparator.

In one aspect, the first energy mode is a cutting mode and the second energy mode is a coagulation mode. In another aspect, the first energy mode is a coagulation mode and the second energy mode is a blend mode. In a further aspect, the first energy mode is a blend mode and the second energy mode is a division with hemostasis mode. In yet another aspect, the first energy mode is a division with hemostasis mode and the second energy mode is a fulguration mode. In another aspect, the first energy mode is a fulguration mode and the second energy mode is a spray mode. In yet another aspect, the first energy mode is a spray mode and the second energy mode is a cutting mode. In yet another aspect, the first energy mode is a continuous energy mode and the second energy mode is a discontinuous energy mode.

In accordance with aspects of the present disclosure, a non-transitory computer-readable storage medium is presented for storing computer-executable instructions which, when executed by a computer, cause the computer to function as an information processing apparatus for a modular electrosurgical generator platform, including a power supply module configured to provide a power input, a first energy module configured to receive the power input and convert the power input into a first energy, and to deliver the first energy represented as a first waveform having a first phase in a first energy mode, a second energy module configured to receive the power input and convert the power input into a second energy, and to deliver the second energy represented as a second waveform having a second phase in a second energy mode, a host controller module configured to control a type and a number of energy modalities provided by the generator platform, a comparator for comparing the first phase of the first energy waveform with the second phase of the second energy waveform in one or more of a plurality of sub-periods, and an adjustment module for adjusting a relative phase between the first and second generators based on results obtained from the comparator.

In one aspect, the adjustment module offsets the first phase from the second phase by a predetermined amount.

In another aspect, the offsetting results in destructive interference of the first and second energy waveforms.

In yet another aspect, the offsetting results in constructive interference of the first and second energy waveforms.

In one aspect, the energy modality is selected from the group consisting of cutting, coagulation, blend, division with hemostasis, fulguration, spray, and combinations thereof.

In another aspect, the first and second energy modules include an RF stage, a sensor stage, a controller stage, and a connector module stage.

In yet another aspect, the RF stage includes an inverter and a preamp.

In one aspect, the modular electrosurgical generator platform supports simultaneous activation of two energy modes.

In another aspect, the host controller module manages requests and controls activation of energy types.

In yet another aspect, the relative phase is adjusted at predefined frequencies.

In accordance with aspects of the present disclosure, a non-transitory computer-readable storage medium is presented for storing a computer-executable program of instructions for causing a computer to perform a method including delivering first energy to a first target tissue via a first generator, the first energy represented as a first waveform having a first phase, delivering second energy to a second target tissue via a second generator, the second energy represented as a second waveform having a second phase, applying the first energy in a first energy mode in a predetermined time period, applying the second energy in a second energy mode in the predetermined time period, comparing the first phase of the first energy waveform with the second phase of the second energy waveform in one or more of a plurality of sub-periods, and adjusting a relative phase between the first and second energy waveforms based on the comparison step.

In one aspect, the adjusting step involves offsetting the first phase from the second phase by a predetermined amount.

In another aspect, the offsetting results in destructive interference of the first and second energy waveforms.

In yet another aspect, the offsetting results in constructive interference of the first and second energy waveforms.

In one aspect, the energy modes are at least one of: bipolar, monopolar, continuous, and discontinuous modes.

In another aspect, at least one modality is selected from the group consisting of cutting, coagulation, blend, division with hemostasis, fulguration, spray, and combinations thereof.

In accordance with aspects of the present disclosure, a non-transitory computer-readable storage medium is presented for storing a computer-executable program of instructions for causing a computer to perform a method including delivering first energy represented as a first waveform via a first surgical instrument to a first target tissue, delivering second energy represented as a second waveform via a second surgical instrument to a second target tissue, comparing the first waveform to the second waveform, and adjusting a relative phase of the first and second waveforms to offset constructive interference.

In one aspect, the comparing step involves comparing zero crossings of the first waveform with zero-crossings of the second waveform to determine the relative phase between the first and second waveforms.

In another aspect, the comparing step involves performing sampling of the first and second waveforms in regions surrounding the zero crossings of the first and second waveforms.

In yet another aspect, sampling data surrounding the zero crossings of the first and second waveforms is provided to a software algorithm for computing the relative phase between the first and second waveforms.

Further scope of applicability of the present disclosure will become apparent from the detailed description given hereinafter. However, it should be understood that the detailed description and specific examples, while indicating illustrative embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

Various embodiments of the subject systems and methods are described herein with reference to the drawings wherein.

The figures depict preferred embodiments of the present disclosure for purposes of illustration only. One skilled in the art will readily recognize from the following detailed description that alternative embodiments of the structures and methods illustrated herein may be employed without departing from the principles of the present disclosure.

DETAILED DESCRIPTION

Reference will now be made in detail to embodiments of the present disclosure. While certain embodiments of the present disclosure will be described, it will be understood that it is not intended to limit the embodiments of the present disclosure to those described embodiments. To the contrary, it will be readily apparent to those skilled in this art that various modifications, rearrangements and substitutions may be made without departing from the spirit of the present disclosure. Further, reference to embodiments of the present disclosure is intended to cover alternatives, modifications, and equivalents as may be included within the spirit and scope of the embodiments of the present disclosure as defined by the appended claims.

Figure 1:
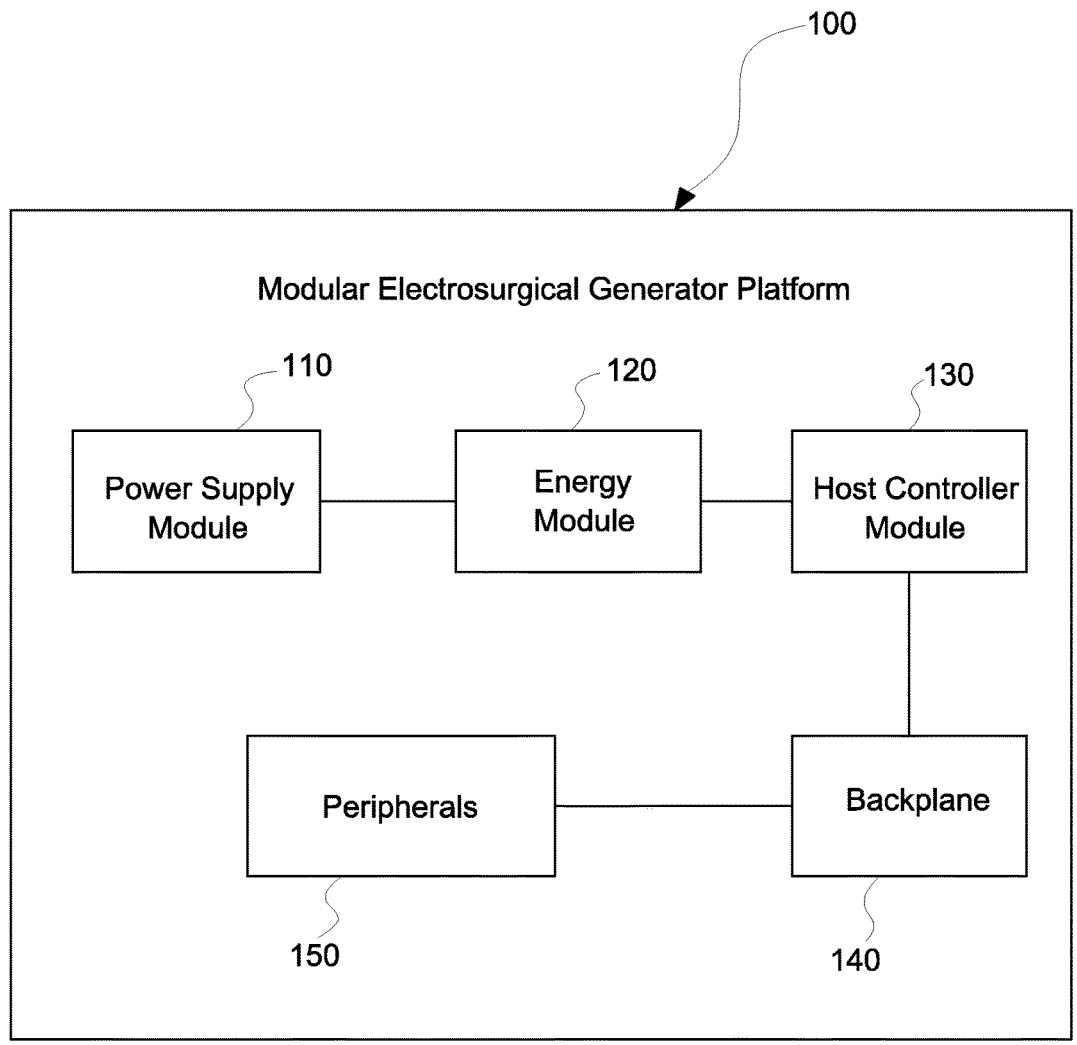
FIG. 1 is a schematic block diagram of a modular electrosurgical generator platform, in accordance with embodiments of the present disclosure.

Referring to FIG. 1, a high-level modular electrosurgical generator platform 100 is presented. The electrosurgical generator platform 100 may include a power supply module 110, an energy module 120, a host controller module 130, a backplane 140, and peripherals 150.

The power supply module 110 powers the energy module 120 with a required power level. The energy module 120 takes input from the power supply module 110 and converts it into therapeutic energy at a frequency between, for example, 400-500 kHz. The backplane 140 may be a fixed circuit board module that receives all sub-modules and carries all signals between sub-modules. The backplane 140 communicates with the host controller module 130 to facilitate with management of the sub-modules. The peripherals 150 may be, for example, footswitches.

Figure 2:
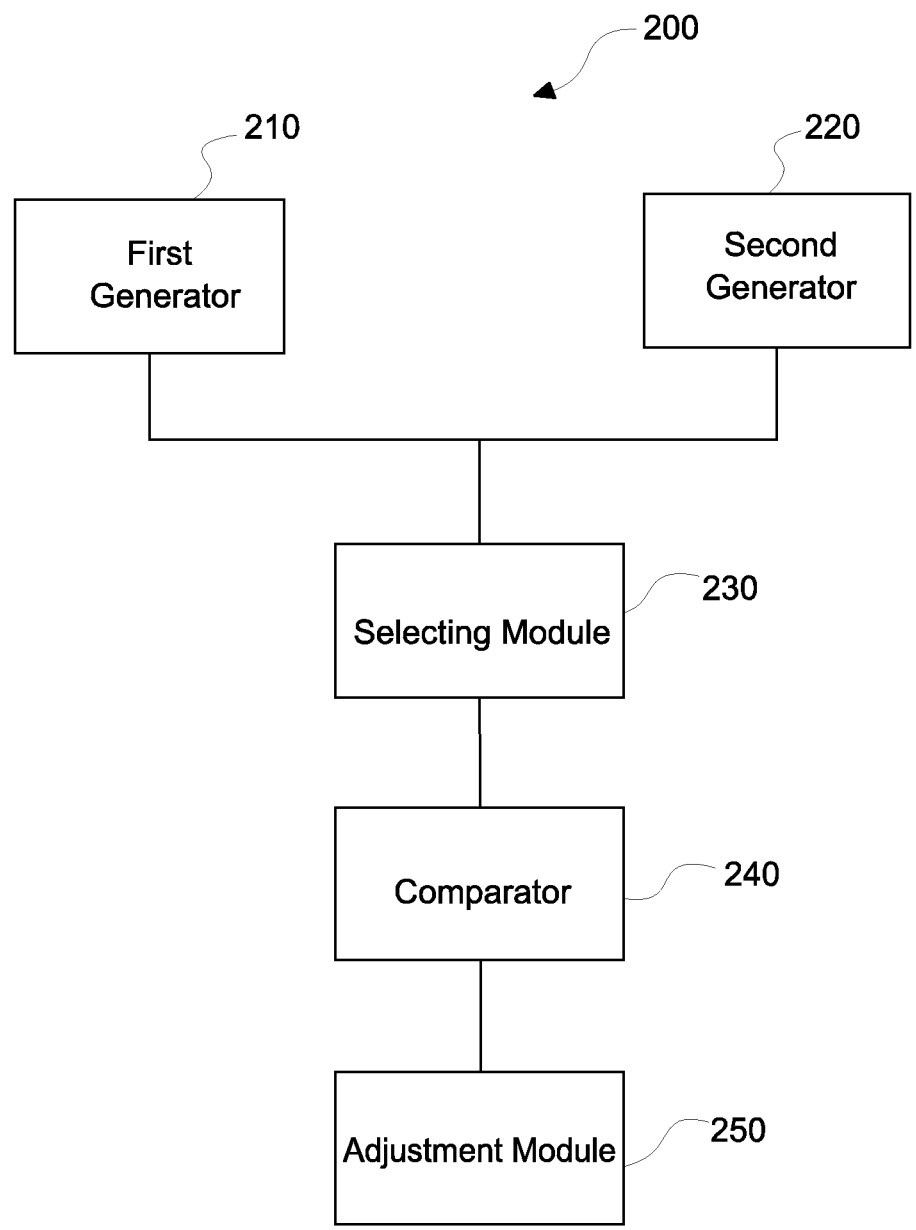
FIG. 2 is a schematic block diagram of a power supply module including two generators, in accordance with an embodiment of the present disclosure.

Referring to FIG. 2, an electrosurgical system 200 may include a first generator 210, a second generator 220, a selecting module 230, a comparator 240, and an adjustment module 250.

Figure 3:
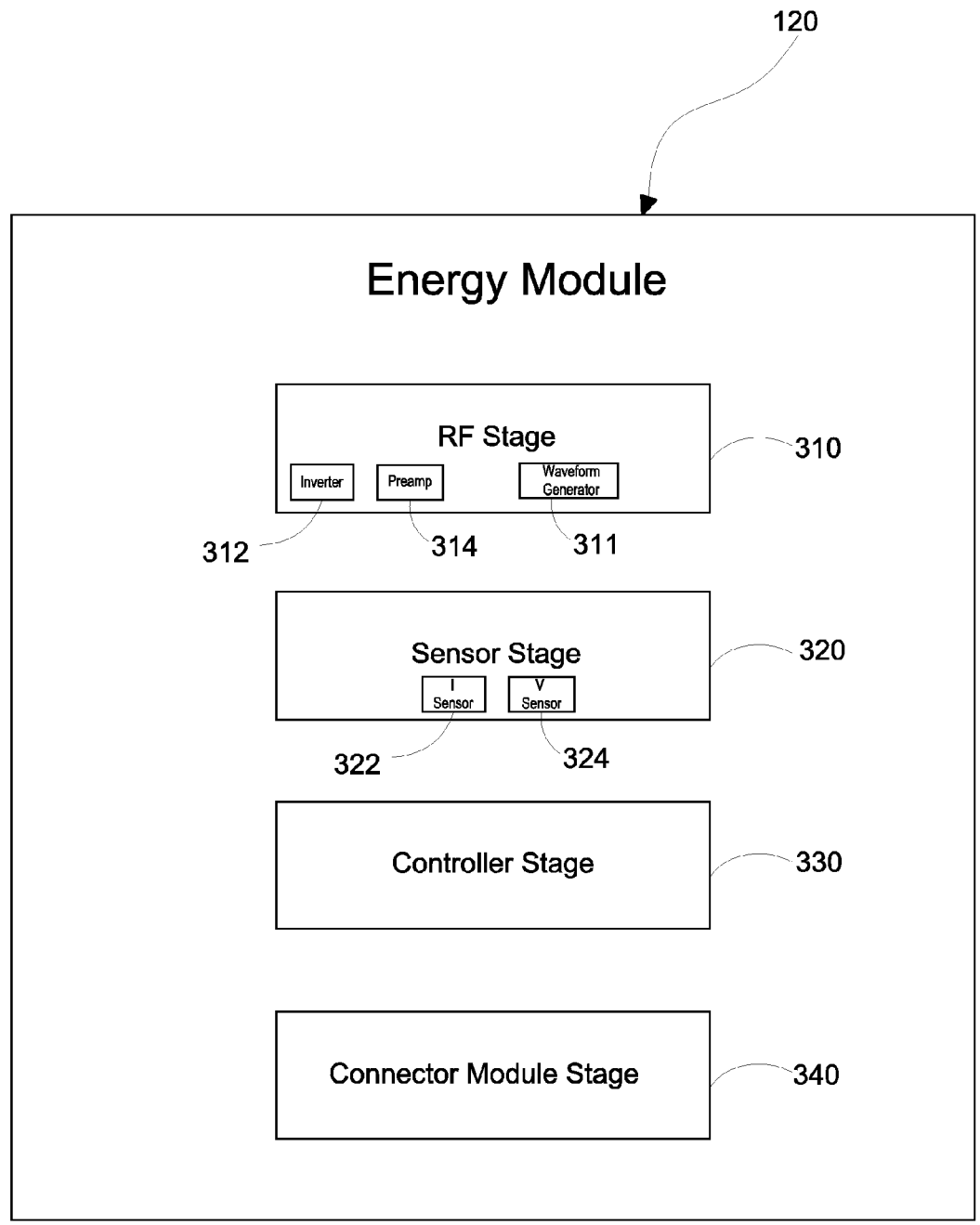
FIG. 3 is a schematic block diagram of an energy module, in accordance with an embodiment of the present disclosure.

Referring to FIG. 3, the energy module 120 may include four different stages. The first stage may be an RF stage 310, the second stage may be a sensor stage 320, the third stage may be a controller stage 330, and the fourth stage may be a connector module stage 340.

The RF stage 310 includes a waveform generator 311, an inverter 312, and a preamp 314. The sensor stage 320 is used to monitor voltage (using voltage sensor 324) and current (using current sensor 322) being delivered to a patient. The controller stage 330 reads the data from sensors 322 and 324, processes the data, and modifies the settings of the RF stage 310 to adjust the power level based on predefined power curves. The connector module stage 340 includes a receptacle allowing connection to compatible instrument plugs. The connector stage module 340 may include, but is not limited to, a barcode scanner to be used for instrument recognition or RFID for the same purpose, as well as a means for insertion detection to determine if an instrument has been fully inserted. Of course, one skilled in the art may contemplate any type of means for instrument recognition. None of the exemplary embodiments described herein are limited to barcodes or RFID recognition.

Figure 4:
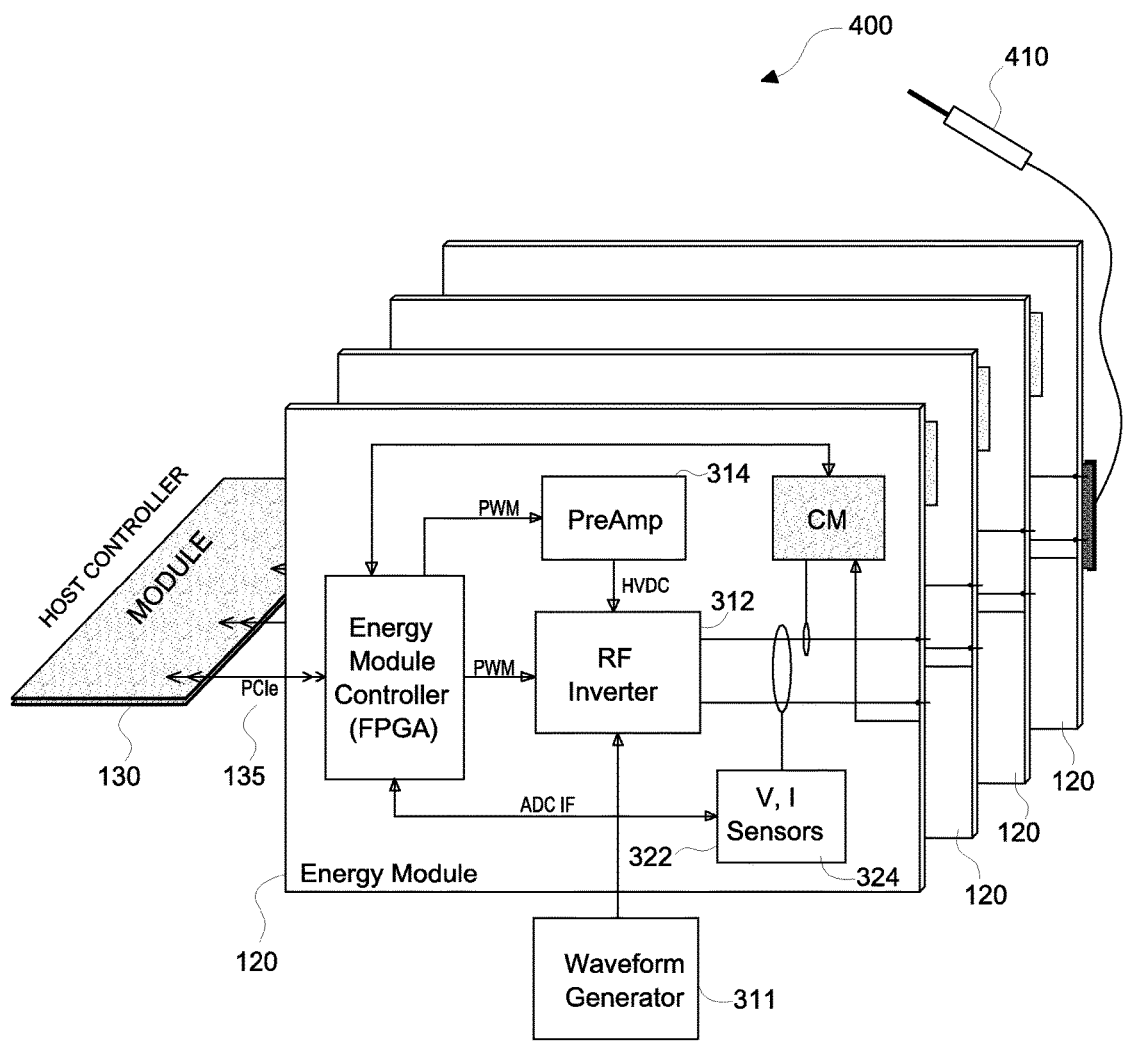
FIG. 4 is a block diagram of a plurality of energy modules connected to a host module, in accordance with an embodiment of the present disclosure.

Referring to FIG. 4, a plurality of energy modules 120 are connected to the host controller module 130. The system 400 may support simultaneous activation of two energy modules 120. It is contemplated that the system 400 may support more than two energy modules 120. The host controller module 130 controls managing the request for energy and the activation of the energy, thus controlling which modules may be simultaneously activated. Each energy module 120 communicates with the host controller module 130 via, for example, a $PCI_e$ bus 135. The $PCI_e$ bus may be selected based on its high speed, low latency, and availability with a plurality of central processing units (CPUs). The energy modules 120 may be connected to a surgical instrument 410.

The host controller module 130 determines the type and number of energy modalities installed in the system, communicates with the energy modules 120, and notifies the energy modules 120 when to provide energy upon receiving an activation request and limits the number of energy modules that can be simultaneously activated. Additionally, the host controller module 130 controls the error handling and communication to the user via, for example, a graphical user interface (GUI) (not shown). The host controller module 130 may also communicate with a hospital network via, for example, a wireless connection. Further, the host controller 130 may also be responsible for managing data storage.

Additionally, the waveform generator 311 is configured to supply PWM signals to the RF inverter 312. The output of RF inverter 312 may be measured by current sensor 322 and voltage sensor 324, which may be bilaterally coupled to an Energy Module Controller (FPGA) of energy module 120.

Figure 5:
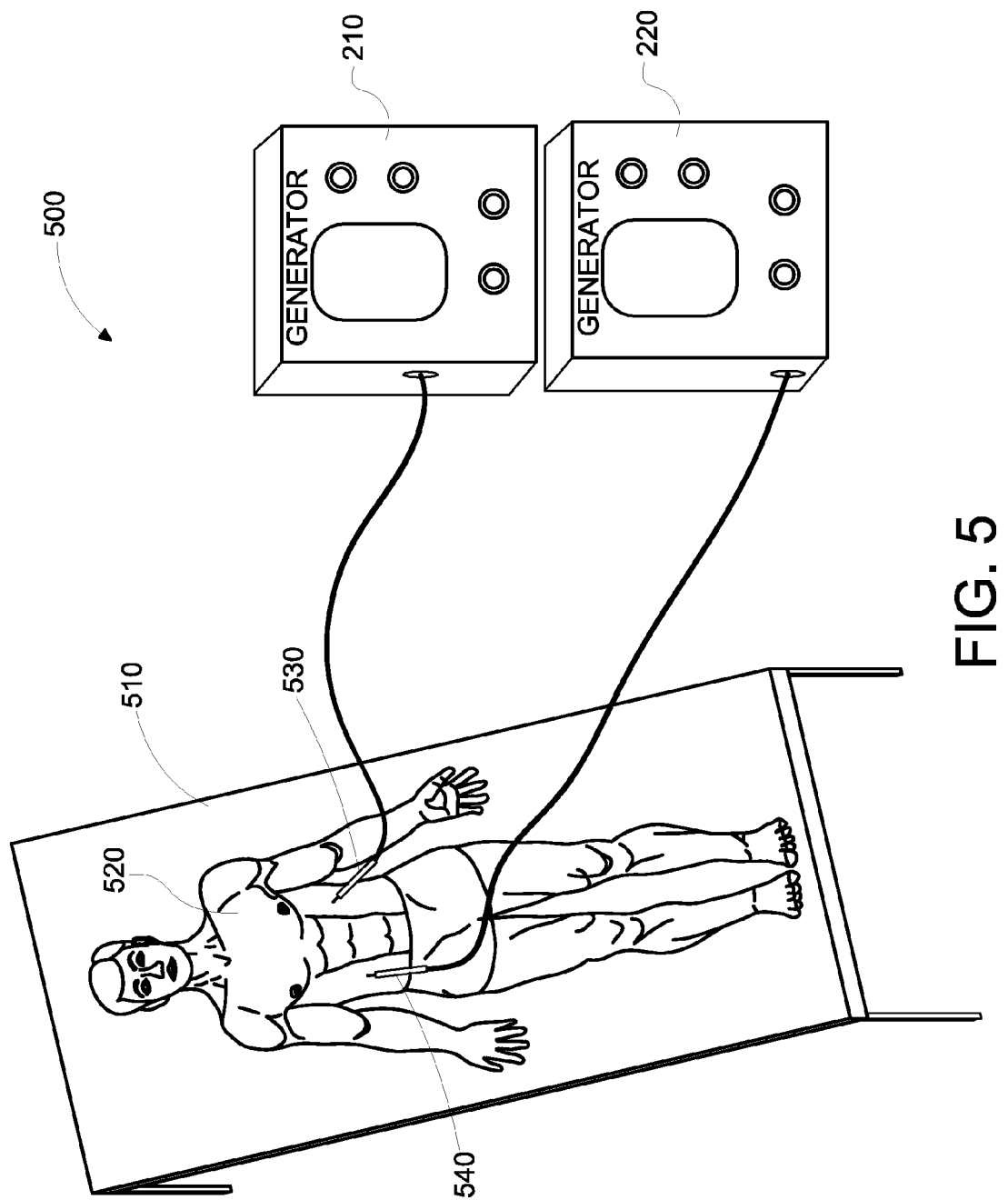
FIG. 5 illustrates an electrosurgical generator connected to two micro-catheters to be inserted into a patient, in accordance with an embodiment of the present disclosure.

Referring to FIG. 5, a system 500 includes electrosurgical generators 210, 220 connected to two surgical instruments 530, 540 (e.g., first and second micro-catheters). The electrosurgical instruments 530, 540 are used during a surgical procedure performed on a patient 520 laying on a table 510 in an operating room. The two electrosurgical instruments 530, 540 may be operated in the same energy modality. However, it is contemplated that the two electrosurgical instruments 530, 540 may also be operated in different modalities. As illustrated in the system 500, during certain surgical procedures, simultaneous intervention at two different sites may be required. Thus, the system 500 has dual channel simultaneous activation capability.

Figure 6:
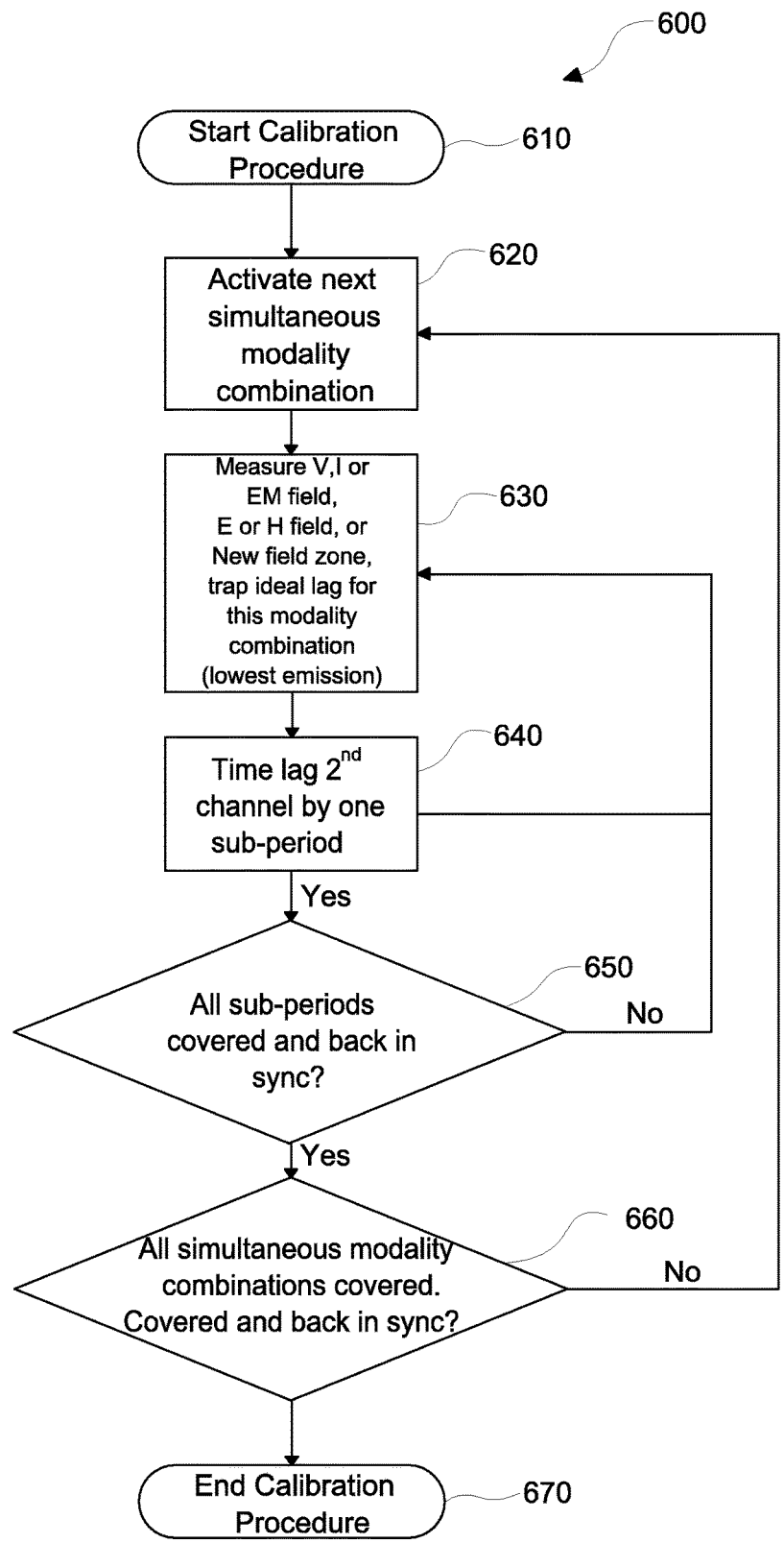
FIG. 6 is a flowchart illustrating a method of executing a calibration procedure, in accordance with an embodiment of the present disclosure.

Referring to FIG. 6, a flowchart 600 illustrating a method of executing a calibration procedure is presented.

The flowchart 600 includes the following steps. In step 610, a calibration procedure is commenced. In step 620, the next simultaneous modality combination is activated. In step 630, the energy emission is measured and an ideal lag time for this modality combination is calculated. The energy emission may be V, I, EM field, E or H field, or near-field zone. In step 640, a time lag is applied to the waveform of the second channel by, for example, one sub-period. In step 650, it is determined whether all sub-periods are covered and are back in sync. If NO, the process proceeds to step 630. If YES, the process proceeds to step 660. In step 660, it is determined whether all the simultaneous modality combinations are covered. If NO, the process proceeds to step 620. If YES, the process proceeds to step 670, where the calibration procedure ends. The process then ends for the first cycle or first iteration. However, the process may be a continuous iterative process. In other words, the steps of the process may repeat for a number cycles or iterations, where the steps are constantly repeated.

Additionally, it is noted that the calibration procedure may occur at the generator after the two devices 530, 540 are plugged in. Alternatively, the calibration procedure may occur by the manufacturer and be stored in the memory of the generators 210, 220 (or first and second energy modules).

With respect to FIGS. 7A-14F, it is shown how one channel is lagged in time with respect to another channel to provide emissive energy reduction at certain frequencies. The amount of time lag may be analog or digitally determined. In the digital domain, each waveform period or repetition cycle is divided into an integer number of sub-periods, which represent a finite length of time. The start of the waveform for the first channel may be lagged by starting the waveform of the second channel at "n," sub-periods later, thus providing a time lag to reduce emissions. A calibration procedure may be developed to "tune" the simultaneous activation by adjusting the time lag between the simultaneous activation waveforms (see FIG. 6 described above).

Moreover, it is noted that the second waveform of the second channel may be delayed for a period of time (e.g., medically insignificant period of time) with respect to the first waveform of the first channel to allow for optimum destructive interference (see FIGS. 7A-14F below). Optimum destructive interference occurs when the first and second waveforms are out-of phase relative to each other by 180°.

Figure 7A:
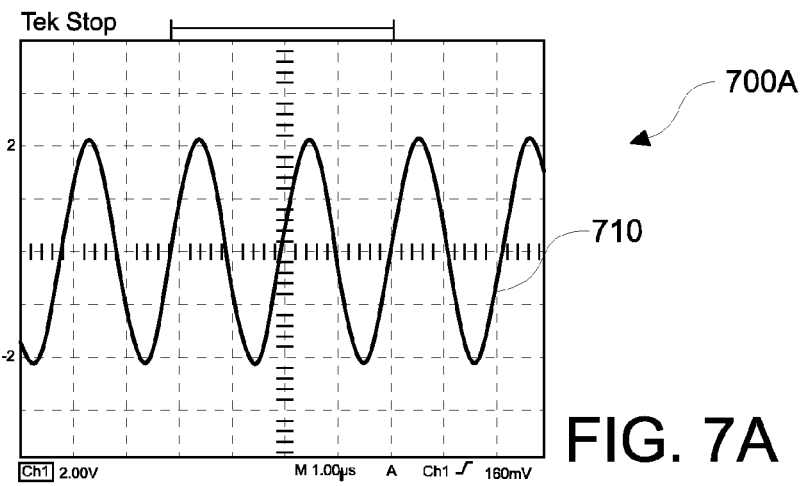
FIGS. 7A-7C are waveforms illustrating constructive interference, according to one aspect of the present disclosure.
Figure 7B:
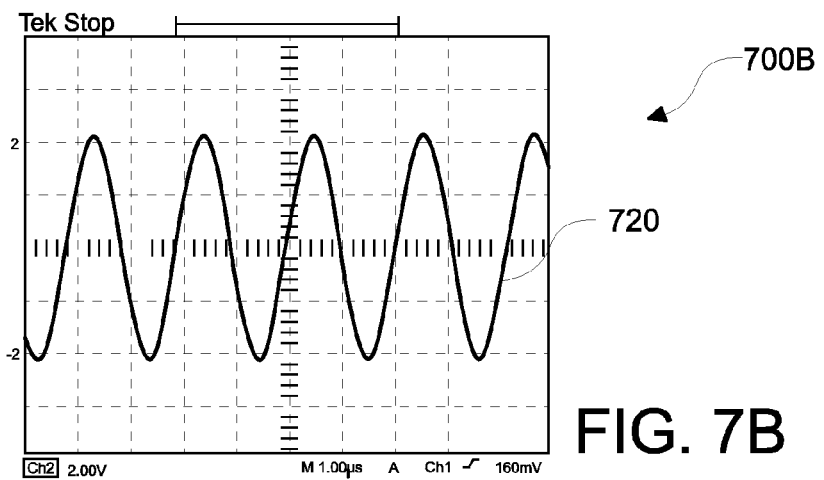
Figure 7C:
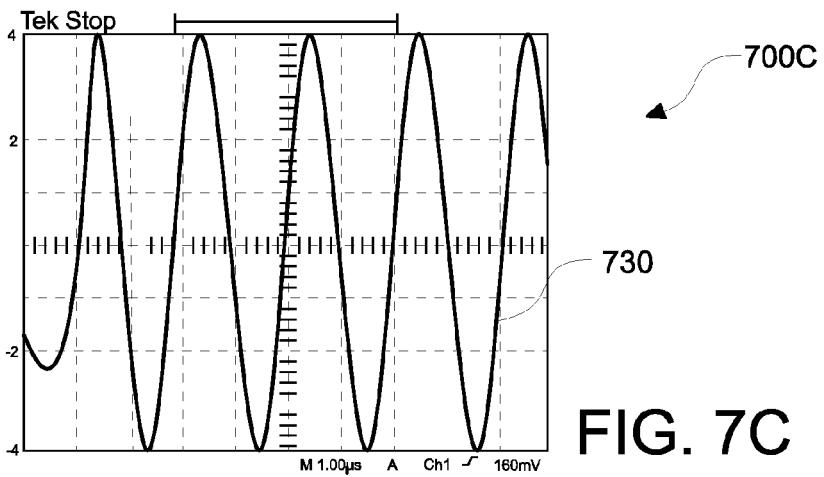

Referring to FIGS. 7A-7C, waveforms illustrating constructive interference are presented. FIG. 7A shows the first channel 700A illustrating a SINE wave 710, whereas FIG. 7B shows the second channel 700B illustrating a SINE wave 720. The SINE wave 710 represents a first energy delivered to a first target tissue via a first generator 210 (see FIG. 5). The SINE wave 720 represents a second energy delivered to a second target tissue via a second generator 220 (see FIG. 5).

It is noted that the first generator 210 may be a first energy module and the second generator 220 may be a second energy module. In other words, the first and second energy modules may be generators, themselves, that draw power from the common backplane 140 (see FIG. 1). Therefore, the term "generator" may be interchangeable with the term "energy module" for certain exemplary embodiments.

FIG. 7C illustrates a waveform resulting from the addition 700C of waveforms 710, 720. As shown, the first waveform 710 has an amplitude of 2V and the second waveform 720 has an amplitude of 2V. The resulting waveform 730 has an amplitude of 4V. In other words, when both surgical instruments 530, 540 (see FIG. 5) are simultaneously used on a patient 520 and the waveforms 710, 720 are in-phase with respect to each other, the energy at all the frequencies is additive, which results in constructive interference.

Interference is a phenomenon in which two waves superimpose to form a resultant wave of greater or lower amplitude. Interference refers to the interaction of waves that are correlated or coherent with each other, either because they come from the same source or because they have the same or nearly the same frequency. The principle of superposition of waves states that when two or more propagating waves of like type are incident on the same point, the total displacement at that point is equal to the vector sum of the displacements of the individual waves. If a crest of a wave coincides with a crest of another wave (i.e., in phase) of the same frequency at the same point, then the magnitude of the displacement is the sum of the individual magnitudes. This is referred to as constructive interference. If a crest of one wave coincides with a trough of another wave (i.e., out of phase) then the magnitude of the displacements is equal to the difference in the individual magnitudes. This is known as destructive interference (see FIGS. 8A-8B below). If the difference between the phases is intermediate between these two extremes, then the magnitude of the displacement of the summed waves lies between the minimum and maximum values.

Thus, in the exemplary embodiments of the present disclosure, the relative phases (between the waveforms) of the respective simultaneous channels are varied such that the emission based additive nature (or constructive interference) of the energy at harmonics is minimized. The term "phase," as used herein, is relative to something else. For example, the term "phase" is used relative to another "waveform," as described relative to FIGS. 7A-14F.

Stated differently, the system of the present disclosure maximizes the destructive interference or keeps the constructive interference within some predetermined maximum value(s). This is applicable to all modes, as well as to a mixture of modes (see FIGS. 13A-14F). The sub-period may be the least common denominator of all of the modes. A software program may be programmed to command the relative phase between the simultaneous waveforms in number of sub-periods to provide emissive energy reduction at certain frequencies. A change in phase (e.g., an optimal time shift) between two waveforms provides different constructive interference and destructive interference effects. The software may include a harmonic minimizer algorithm.

Figure 8A:
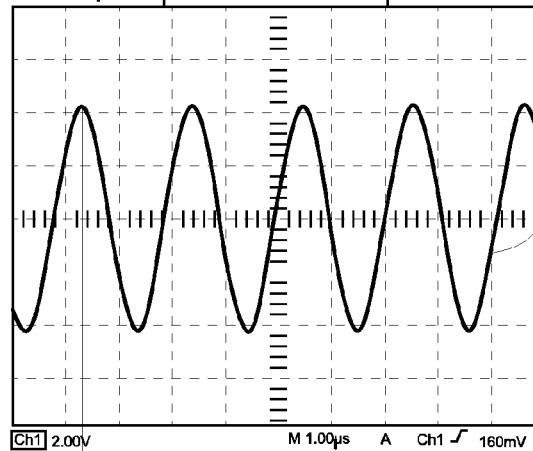
FIGS. 8A-8C are waveforms illustrating partial constructive interference, according to one aspect of the present disclosure.
Figure 8B:
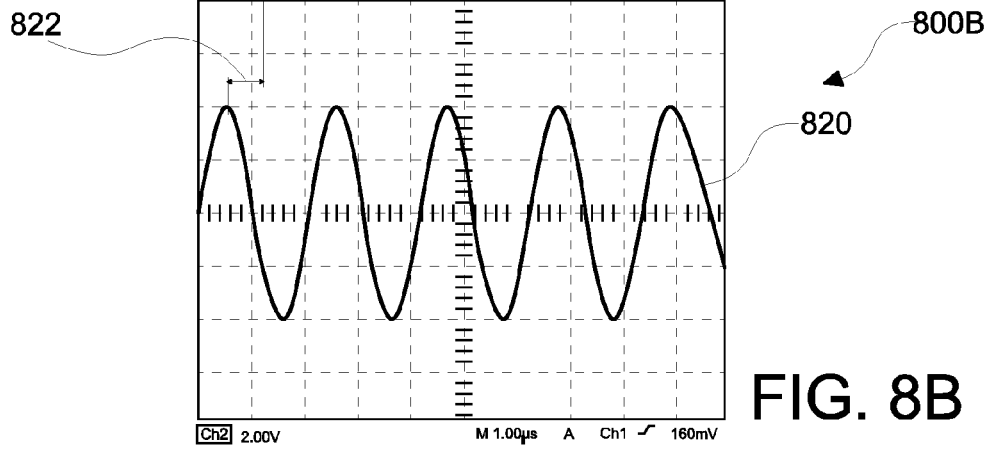
Figure 8C:
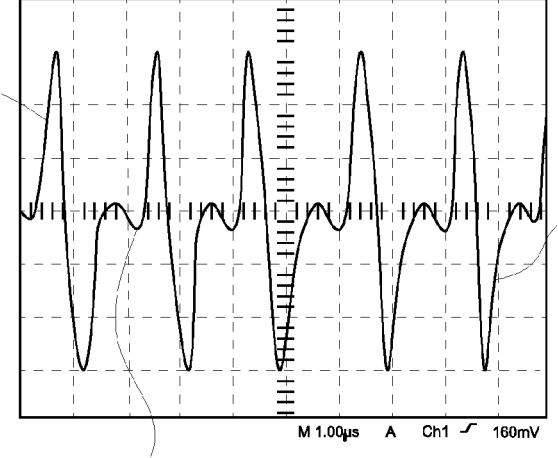

Referring to FIGS. 8A-8C, waveforms illustrating partial constructive interference are presented. FIG. 8A shows the first channel 800A illustrating a SINE wave 810, whereas FIG. 7B shows the second channel 800B illustrating a SINE wave 820. The SINE wave 810 represents a first energy delivered to a first target tissue via a first generator 210 (see FIG. 5). The SINE wave 820 represents a second energy delivered to a second target tissue via a second generator 220 (see FIG. 5). FIG. 8C illustrates a waveform resulting from the addition 800C of waveforms 810, 820. As shown, the first waveform 810 has an amplitude of 2V and the second waveform 820 has an amplitude of 2V. However, the resulting waveform 830 does not have an amplitude of 4V at every crest or peak. In other words, when both surgical instruments 530, 540 (see FIG. 5) are simultaneously used on a patient 520 and the waveforms 810, 820 are out-of-phase (or out of sync) with respect to each other by a time distance shown as 822 in FIG. 8B, the energy at some of the frequencies is additive, whereas the energy at some of the frequencies is subtractive, thus resulting in partial constructive/destructive interference at select points.

For example, wave portion 835 illustrates the additive nature of the waveforms 810, 820, whereas wave portion 837 illustrates the subtractive nature of the waveforms 810, 820. When both surgical instruments 530, 540 (see FIG. 5) are simultaneously used on a patient 520, it is desired to create as much destructive interference of the waveforms 810, 820 as possible. In order to accomplish this, a first energy is applied in a first energy mode at a predetermined time period and a second energy is applied in a second energy mode at the predetermined time period. A plurality of sub-periods may then be selected in that predetermined time period. Then a first phase of the first waveform 810 is compared to a second phase of the second waveform 820 in one or more of the plurality of predetermined sub-periods. A relative phase between the waveforms of the first and second generators 210, 220 (or first and second energy modules) is then adjusted based on the comparison step in order to create more destructive interference. The adjusting step involves offsetting the first phase from the second phase (between waveforms) by a predetermined amount to produce different destructive interference effects based on the selected modes of operation of each surgical instrument 530, 540. The relative phase between waveforms may also be adjusted at certain predefined frequencies. The relative phase between waveforms is varied by software to optimize a time shift. The waveform is shifted by a carrier frequency. The source of the carrier frequency is a set of PWM signals that are sent into the RF inverter component for FET switching. The set of PWM signals are time-shifted by a specified sub-period amount.

Figure 8D:
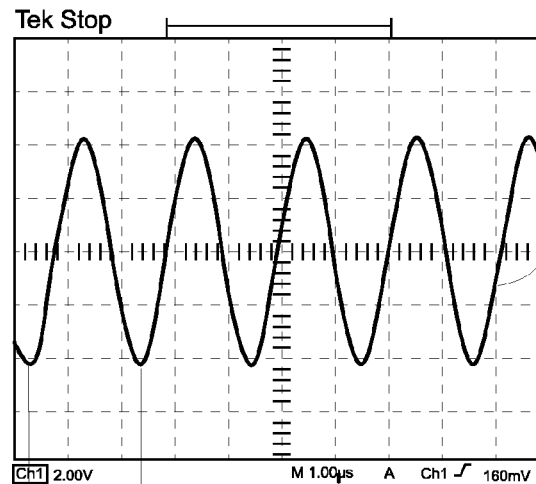
FIGS. 8D-8F are waveforms illustrating complete destructive interference (i.e., 180° out-of-phase between waveforms), according to one aspect of the present disclosure.
Figure 8E:
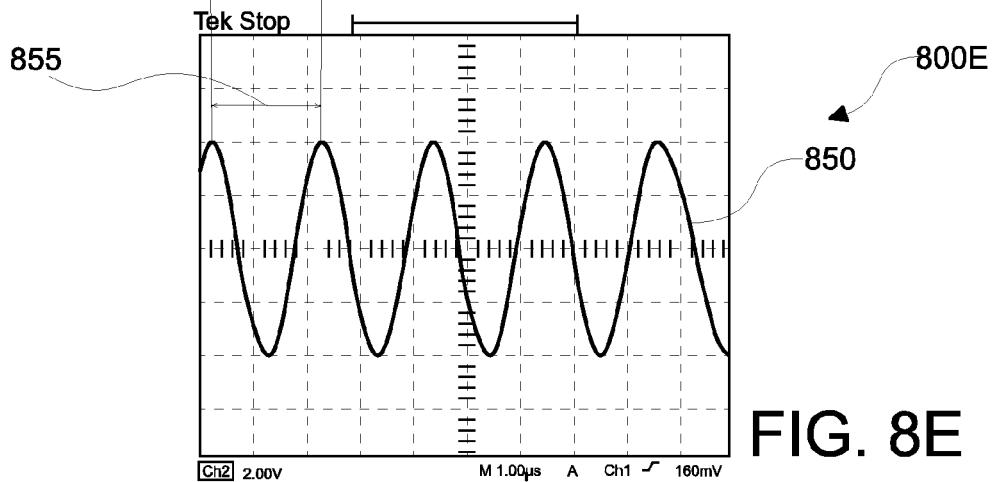
Figure 8F:
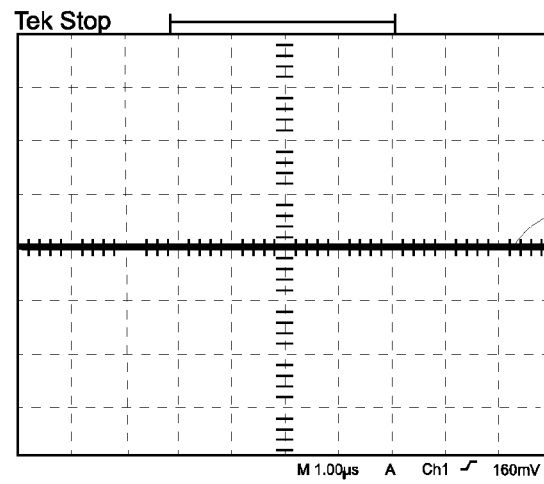

FIGS. 8D-8F are waveforms illustrating complete destructive interference (i.e., 180° out-of-phase between waveforms), according to one aspect of the present disclosure.

FIG. 8D shows a first channel 800D illustrating a first waveform 840, whereas FIG. 8E shows a second channel 800E illustrating a second waveform 850 that is out-of-phase with the first waveform 840 by 180°. FIG. 8F illustrates a waveform resulting from the addition of first and second waveforms 840, 850. Waveform 860 illustrates complete destructive interference that results from the additions of waveforms 840, 850. As a result, waveform 860 has an amplitude of 0° and extends along the x-axis. In other words, when both surgical instruments 530, 540 (see FIG. 5) are simultaneously used on a patient 520 and the waveforms 840, 850 are out-of-phase by a time distance shown as 855 in FIG. 8E, the energy at all of the frequencies is subtractive, thus resulting in complete destructive interference.

One objective of the partial or complete destructive interference is to lower the E field or the H field or the EM field to the surgeon or patient or support staff near the surgical site. Additionally, all the waveforms illustrated in FIGS. 8A-8F may be representative of voltage (V) or current (I) or radiated RF (V/m, A/m or power density, such as mW/cm$^2$).

Figure 9A:
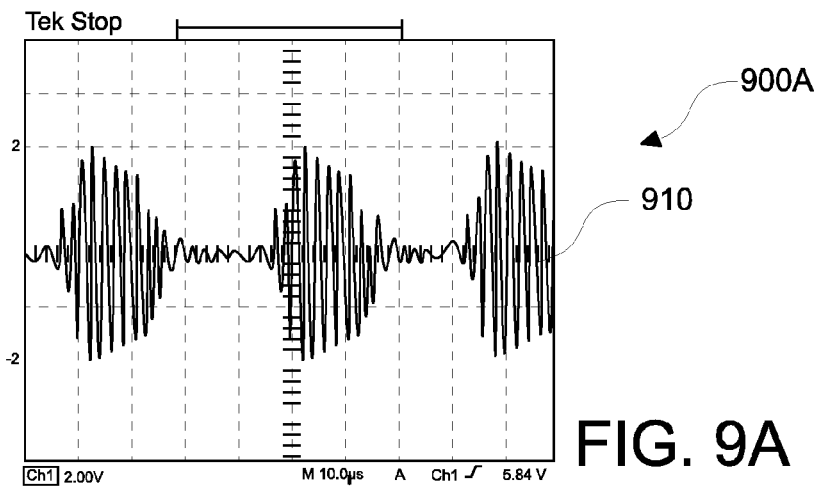
FIGS. 9A-9C are blend mode waveforms illustrating constructive interference, according to one aspect of the present disclosure.
Figure 9B:
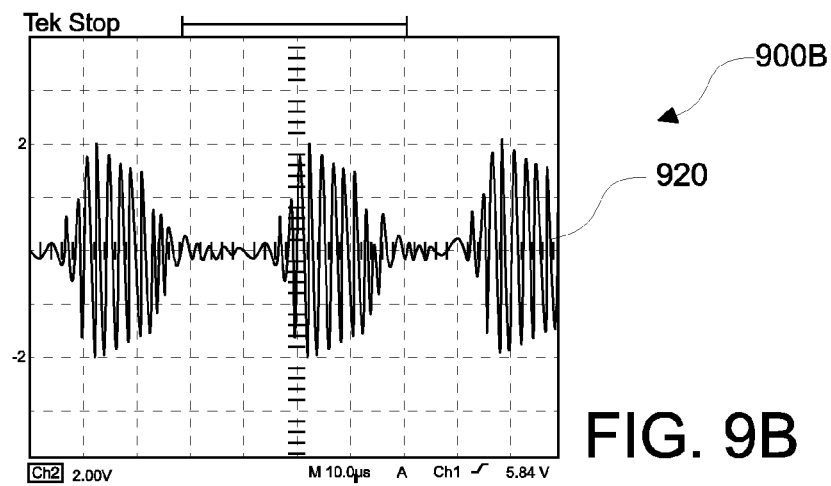
Figure 9C:
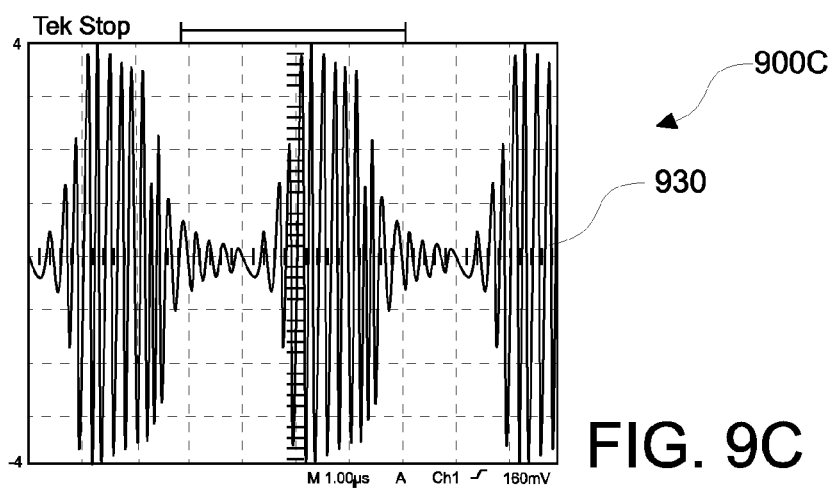

Referring to FIGS. 9A-9B, waveforms illustrating constructive interference are presented for a blend mode. FIG. 9A shows the first channel 900A illustrating a wave 910, whereas FIG. 9B shows the second channel 900B illustrating a wave 920. The wave 910 represents a first energy delivered to a first target tissue via a first generator 210 (see FIG. 5). The wave 920 represents a second energy delivered to a second target tissue via a second generator 220 (see FIG. 5). FIG. 9C illustrates a waveform resulting from the addition 900C of waveforms 910, 920. As shown, the first waveform 910 has an amplitude of 2V and the second waveform 920 has an amplitude of 2V. The resulting waveform 930 has an amplitude of 4V. In other words, when both surgical instruments 530, 540 (see FIG. 5) are simultaneously used on a patient 520 and the waveforms 910, 920 are in-phase, the energy at all the frequencies is additive, which results in constructive interference. This situation is desired to be avoided by providing at least one waveform out-of-phase (or out of sync) with respect to the other waveform, as shown in FIGS. 10A-10C.

Figure 10A:
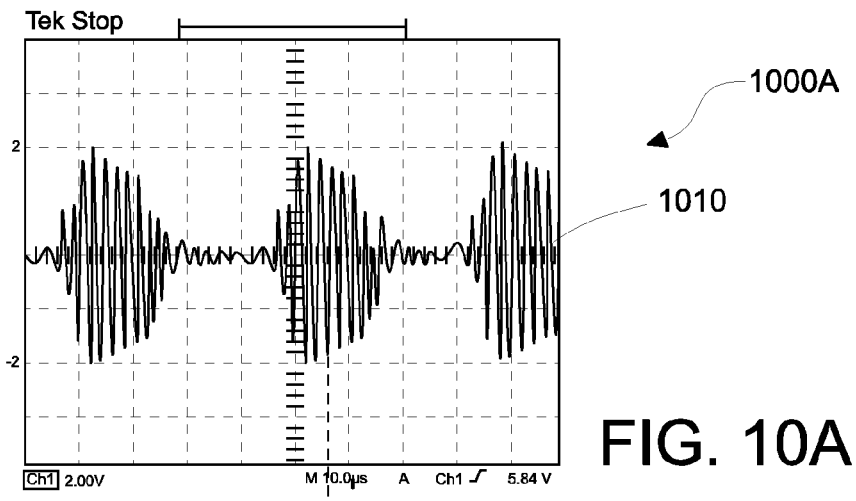
FIGS. 10A-10C are blend mode waveforms illustrating partial constructive interference, according to one aspect of the present disclosure.
Figure 10B:
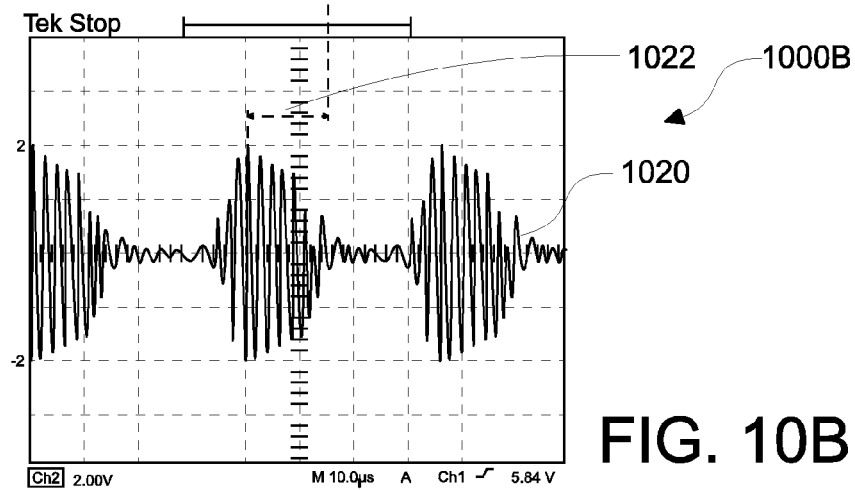
Figure 10C:
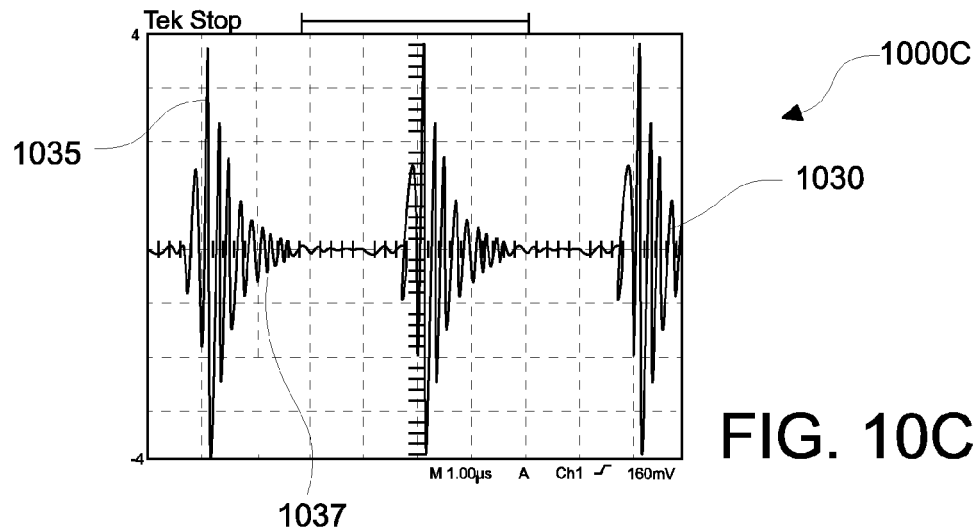

Referring to FIGS. 10A-10C, waveforms illustrating partial constructive interference are presented. FIG. 10A shows the first channel 1000A illustrating a wave 1010, whereas FIG. 10B shows the second channel 1000B illustrating a wave 1020. The wave 1010 represents a first energy delivered to a first target tissue via a first generator 210 (see FIG. 5). The wave 1020 represents a second energy delivered to a second target tissue via a second generator 220 (see FIG. 5). FIG. 10C illustrates a waveform resulting from the addition 1000C of waveforms 1010, 1020. As shown, the first waveform 1010 has an amplitude of 2V and the second waveform 1020 has an amplitude of 2V. However, the resulting waveform 1030 does not have an amplitude of 4V at every crest or peak. In other words, when both surgical instruments 530, 540 (see FIG. 5) are simultaneously used on a patient 520 and the waveforms 1010, 1020 are out-of-phase (or out of sync) by a distance shown as 1022 in FIG. 10B, the energy at some of the frequencies is additive, whereas the energy at some of the frequencies is subtractive, thus resulting in at least some constructive/destructive interference at certain points.

For example, wave portion 1035 illustrates the additive nature of the waveforms 1010, 1020, whereas wave portion 1037 illustrates the subtractive nature of the waveforms 1010, 1020. When both surgical instruments 530, 540 (see FIG. 5) are simultaneously used on a patient 520, it is desired to create as much destructive interference of the waveforms 1010, 1020 as possible, in order to simultaneously operate both surgical instruments 530, 540 in a blend mode. In order to accomplish this, a first energy is applied in a first energy mode at a predetermined time period and a second energy is applied in a second energy mode at the predetermined time period, where the first and second energy modes are the same. A plurality of sub-periods may then be selected in that predetermined time period. Then a first phase of the first waveform 1010 is compared to a second phase of the second waveform 1020 in one or more of the plurality of predetermined sub-periods. A relative phase between the first and second generators 210, 220 (or energy modules) is then adjusted based on the comparison step in order to create more destructive interference. The adjusting step involves offsetting the first phase from the second phase by a predetermined amount to produce different destructive interference effects based on the selected modes of operation of each surgical instrument 530, 540. The relative phase may also be adjusted at certain predefined frequencies.

Figure 10D:
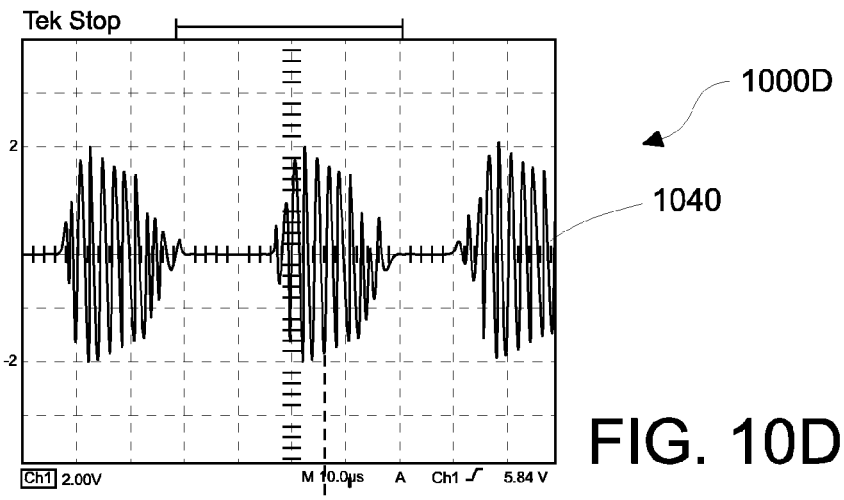
FIGS. 10D-10F are waveforms illustrating no constructive interference according to one aspect of the present disclosure.
Figure 10E:
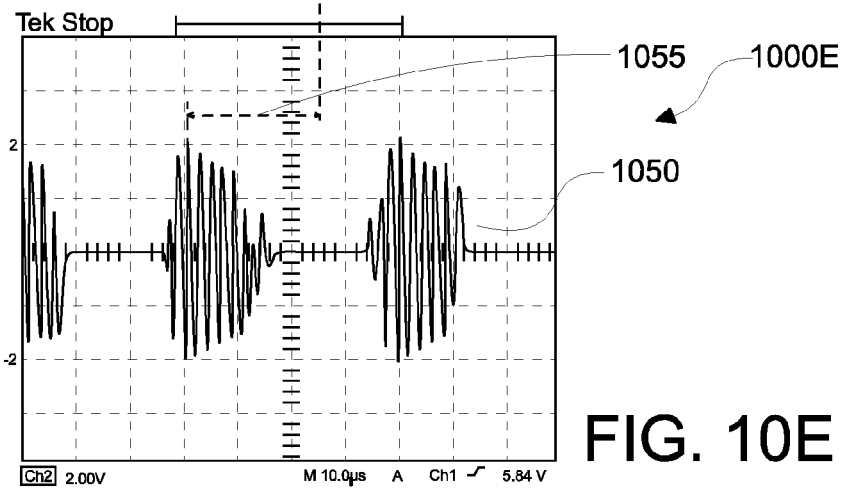
Figure 10F:
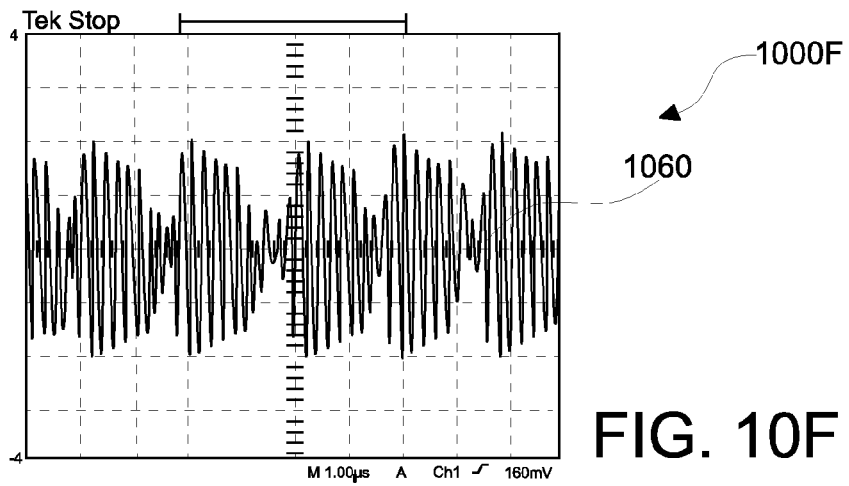

FIGS. 10D-10F are waveforms illustrating no constructive interference, according to one aspect of the present disclosure.

FIG. 10D shows a first channel 1000D illustrating a first waveform 1040, whereas FIG. 10E shows a second channel 1000E illustrating a second waveform 1050 that is out-of-phase with the first waveform 1040 by 180°. FIG. 10F illustrates a waveform resulting from the addition 1000F of first and second waveforms 1040, 1050. Waveform 1060 illustrates no constructive interference that results from the additions of waveforms 1040, 1050. As a result, waveform 1060 has an amplitude of 0° and extends along the x-axis. In other words, when both surgical instruments 530, 540 (see FIG. 5) are simultaneously used on a patient 520 and the waveforms 1040, 1050 are out-of-phase by a time distance shown as 1055 in FIG. 10E, and the energy at all frequencies results in no constructive interference.

One objective of the partial or complete destructive interference is to lower the E field or the H field or the EM field to the surgeon or patient or support staff near the surgical site. Additionally, all the waveforms illustrated in FIGS. 10A-10F may be representative of voltage (V) or current (I) or radiated RF (V/m, A/m or power density, such as mW/cm$^2$).

Figure 11A:
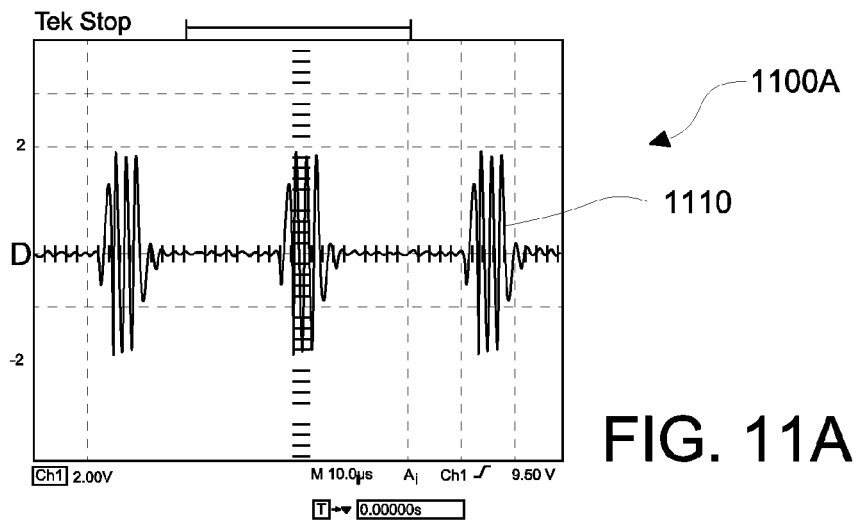
FIGS. 11A-11C are coag-driven waveforms, illustrating constructive interference, according to one aspect of the present disclosure.
Figure 11B:
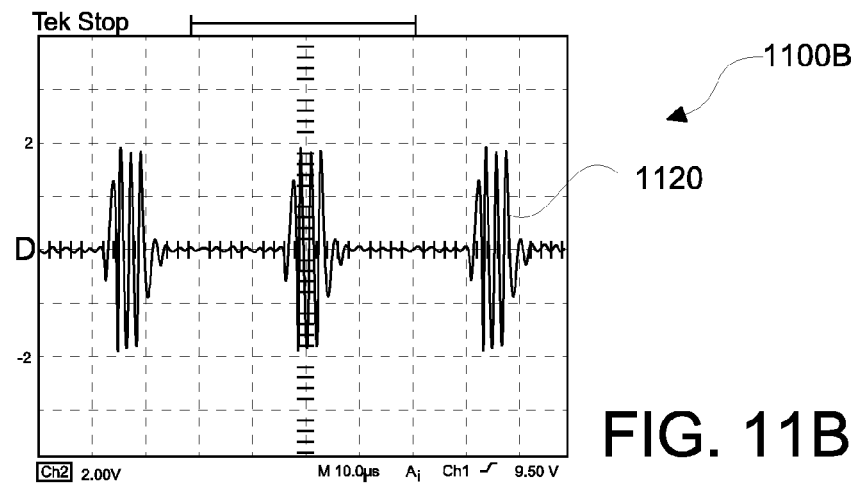
Figure 11C:
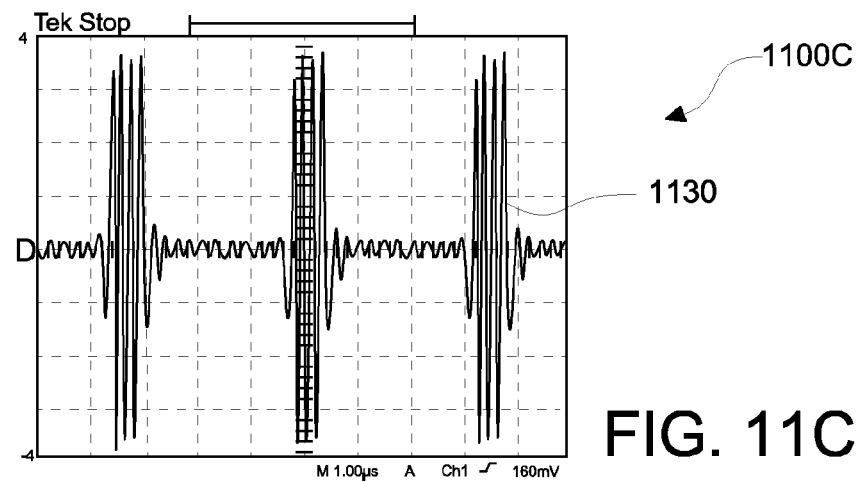

Referring to FIGS. 11A-11B, waveforms illustrating constructive interference are presented for a coag-driven mode. FIG. 11A shows the first channel 1100A illustrating a wave 1110, whereas FIG. 11B shows the second channel 1100B illustrating a wave 1120. The wave 1110 represents a first energy delivered to a first target tissue via a first generator 210 (see FIG. 5). The wave 1120 represents a second energy delivered to a second target tissue via a second generator 220 (see FIG. 5). FIG. 11C illustrates a waveform resulting from the addition 1100C of waveforms 1110, 1120. As shown, the first waveform 1110 has an amplitude of 2V and the second waveform 1120 has an amplitude of 2V. The resulting waveform 1130 has an amplitude of 4V. In other words, when both surgical instruments 530, 540 (see FIG. 5) are simultaneously used on a patient 520 and the waveforms 1110, 1120 are in-phase, the energy at all the frequencies is additive, which results in constructive interference. This situation is desired to be avoided by providing at least one waveform out-of-phase (or out of sync) with respect to the other waveform, as shown in FIGS. 12A-12C.

Figure 12A:
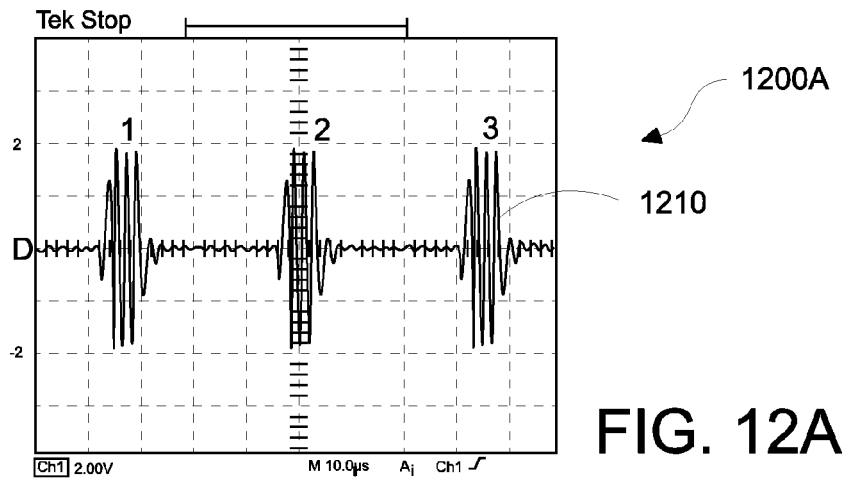
FIGS. 12A-12C are coag-driven waveforms, which provide dissection with hemostasis, illustrating partial or incomplete destructive interference, according to one aspect of the present disclosure.
Figure 12B:
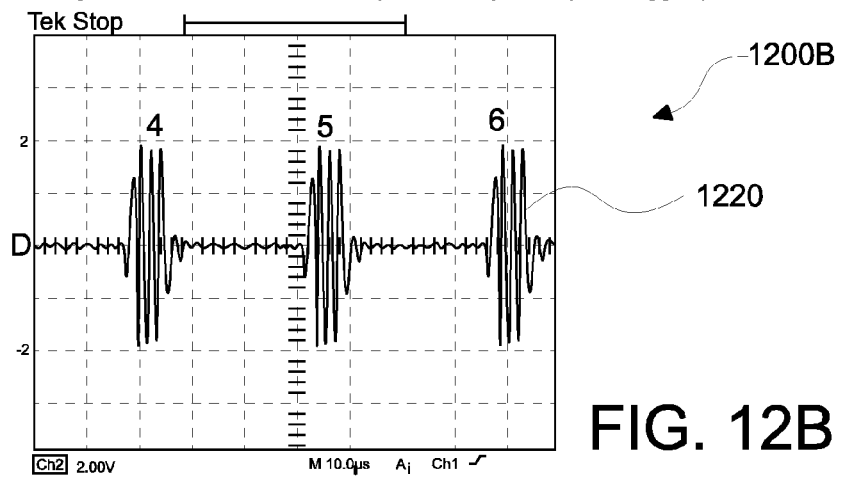
Figure 12C:
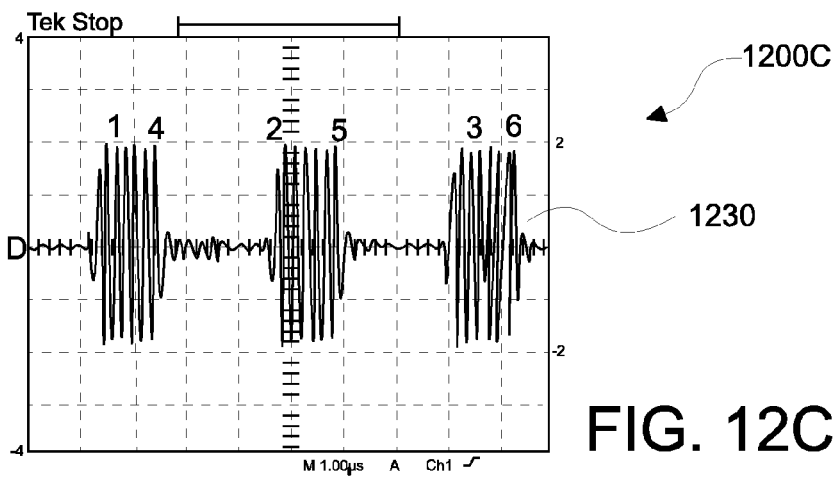

Referring to FIGS. 12A-12C, waveforms illustrating partial or incomplete destructive interference are presented. FIG. 12A shows the first channel 1200A illustrating a wave 1210, whereas FIG. 12B shows the second channel 1200B illustrating a wave 1220. The wave 1210 represents a first energy delivered to a first target tissue via a first generator 210 (see FIG. 5). The wave 1220 represents a second energy delivered to a second target tissue via a second generator 220 (see FIG. 5). FIG. 12C illustrates a waveform resulting from the addition 1200C of waveforms 1210, 1220. As shown, the first waveform 1210 has an amplitude of 2V and the second waveform 1220 has an amplitude of 2V. However, the resulting waveform 1230 does not have an amplitude of 4V at every crest or peak. In other words, when both surgical instruments 530, 540 (see FIG. 5) are simultaneously used on a patient 520 and the waveforms 1210, 1220 are out-of-phase (or out of sync), such that the energy at all the frequencies is subtractive, thus resulting in partial destructive interference.

For example, waveform 1210 includes three SINE wave portions 1, 2, 3, whereas waveform 1220 includes four SINE wave portions 4, 5, 6, 7. The SINE wave portions 1, 2, 3 are out-of-phase (or out of sync) with respect to the four SINE wave portions 4, 5, 6, 7. Therefore, in FIG. 12C, when waveforms 1210, 1200 are added, there is no constructive interference and the peaks or crests of all the SINE wave portions 1-7 are maintained within a band or region that is less than 2V.

Figure 12D:
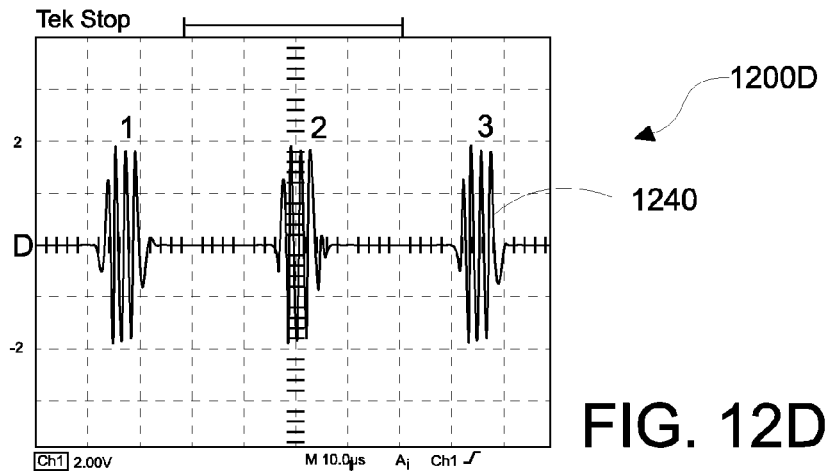
FIGS. 12D-12F are waveforms illustrating no constructive interference according to one aspect of the present disclosure.
Figure 12E:
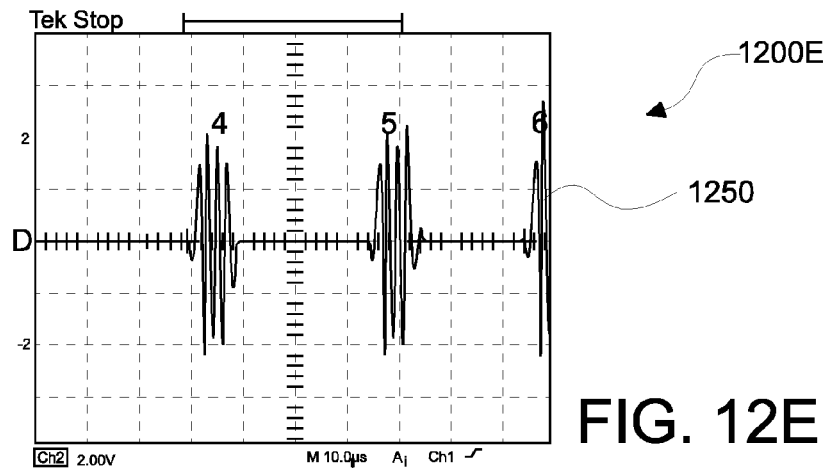
Figure 12F:
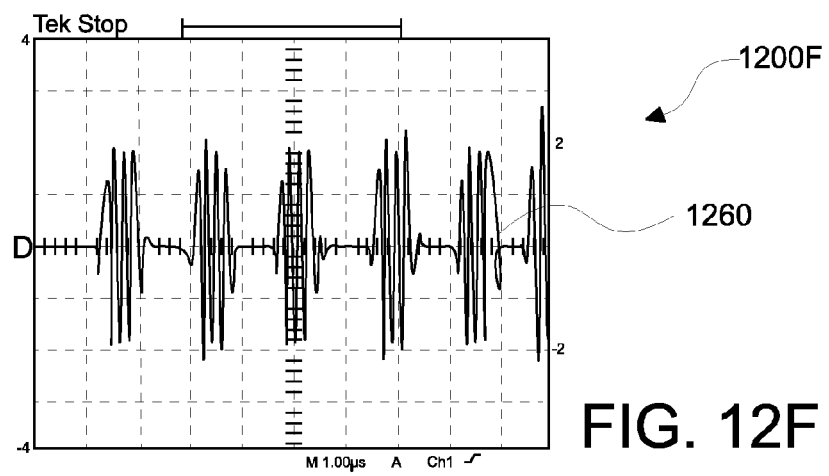

FIGS. 12D-12F are waveforms illustrating no constructive interference, according to one aspect of the present disclosure.

FIG. 12D shows a first channel 1200D illustrating a first waveform 1240, whereas FIG. 12E shows a second channel 1200E illustrating a second waveform 1250 that is out-of-phase with the first waveform 1240 by 180°. FIG. 12F illustrates a waveform resulting from the addition 1200F of first and second waveforms 1240, 1250. Waveform 1260 illustrates no constructive interference that results from the additions of waveforms 1240, 1250. As a result, waveform 1260 has an amplitude of 0° and extends along the x-axis. In other words, when both surgical instruments 530, 540 (see FIG. 5) are simultaneously used on a patient 520 and the waveforms 1240, 1250 are out-of-phase by 180°, and the energy at all frequencies results in no constructive interference.

One objective of the partial or complete destructive interference is to lower the E field or the H field or the EM field to the surgeon or patient or support staff near the surgical site. Additionally, all the waveforms illustrated in FIGS. 12A-12F may be representative of voltage (V) or current (I) or radiated RF (V/m, A/m or power density, such as mW/cm$^2$).

Figure 13A:
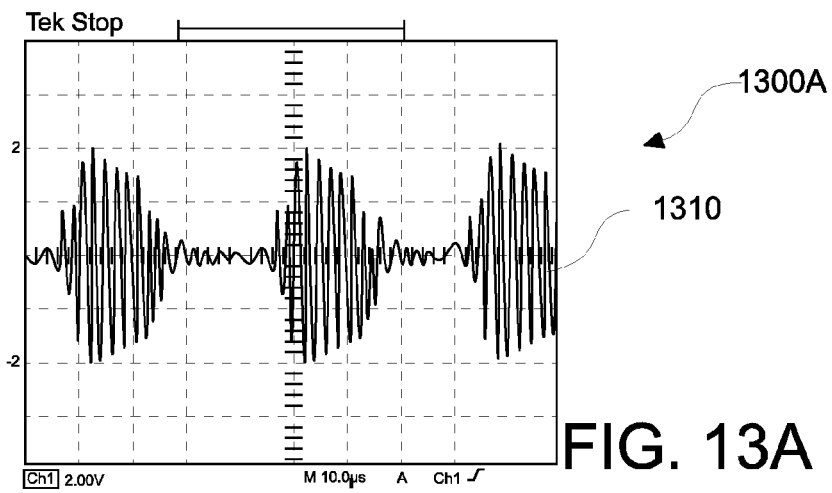
FIGS. 13A-13C are two waveforms of different modalities illustrating constructive interference, according to one aspect of the present disclosure.
Figure 13B:
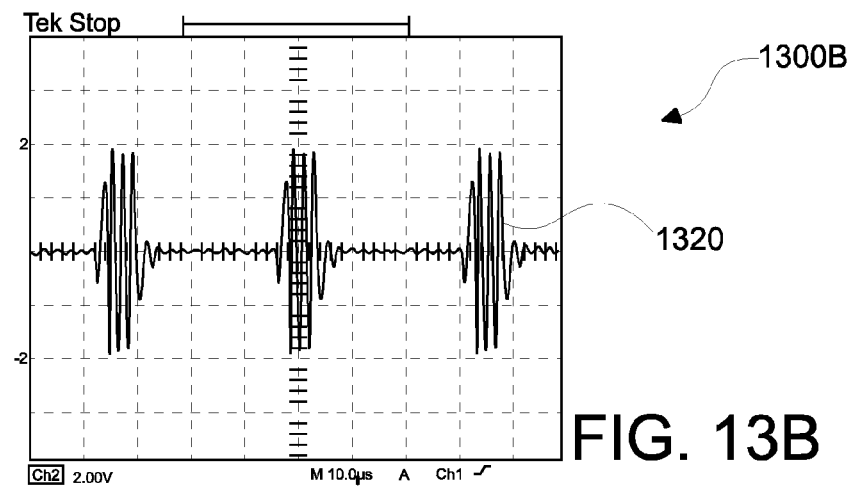
Figure 13C:
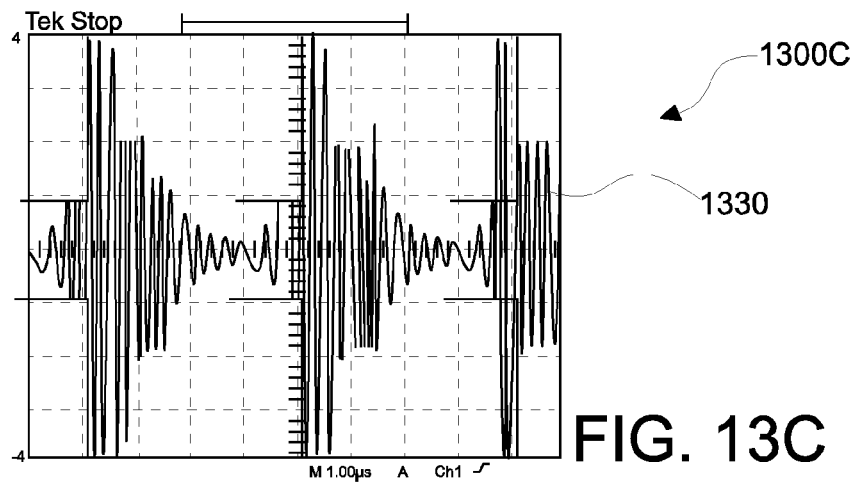

Referring to FIGS. 13A-13B, waveforms illustrating constructive interference are presented for a mixed mode of operation. FIG. 13A shows the first channel 1300A illustrating a wave 1310 operating in a blend mode, whereas FIG. 13B shows the second channel 1300B illustrating a wave 1320 operating in a coag-driven. The wave 1310 represents a first energy delivered to a first target tissue via a first generator 210 (see FIG. 5). The wave 1320 represents a second energy delivered to a second target tissue via a second generator 220 (see FIG. 5). FIG. 13C illustrates a waveform resulting from the addition 1300C of waveforms 1310, 1320. As shown, the first waveform 1310 has an amplitude of 2V and the second waveform 1320 has an amplitude of 2V. The resulting waveform 1330 has an amplitude of 4V. In other words, when both surgical instruments 530, 540 (see FIG. 5) are simultaneously used on a patient 520 and the waveforms 1310, 1320 are in-phase, the energy at certain frequencies is additive, which results in constructive interference. This situation is desired to be avoided by providing at least one waveform out-of-phase (or out of sync) with respect to the other waveform, as shown in FIGS. 14A-14C.

Figure 14A:
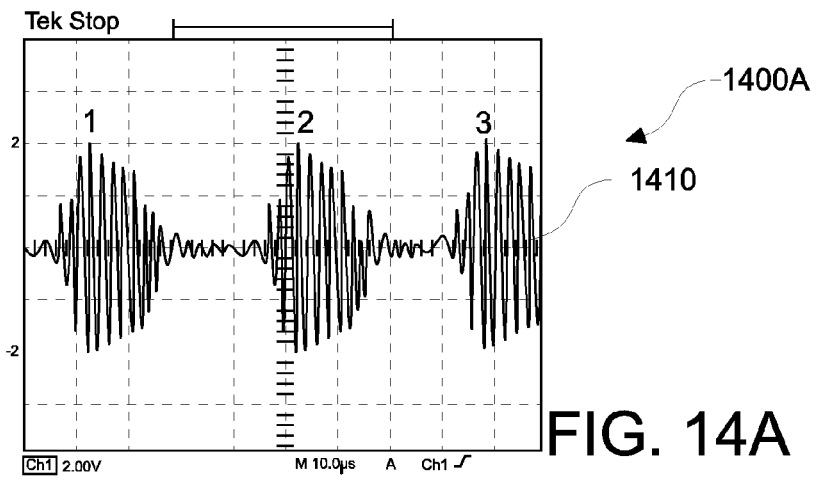
FIGS. 14A-14C are two waveforms of different modalities illustrating partial or incomplete destructive interference, according to one aspect of the present disclosure.
Figure 14B:
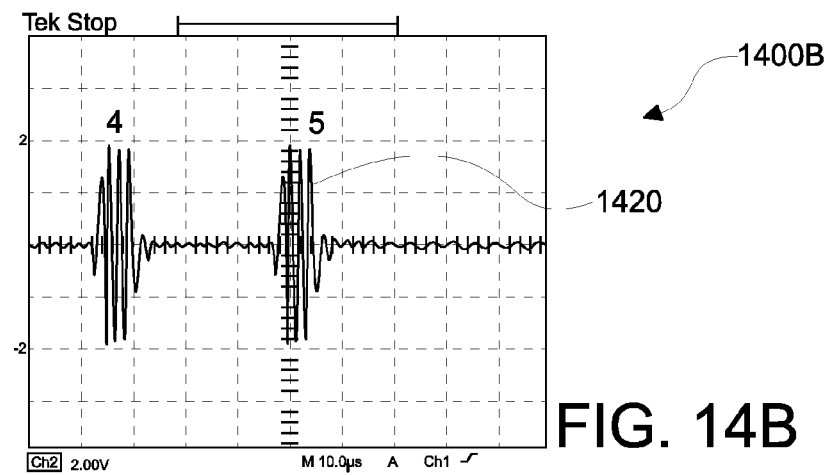
Figure 14C:
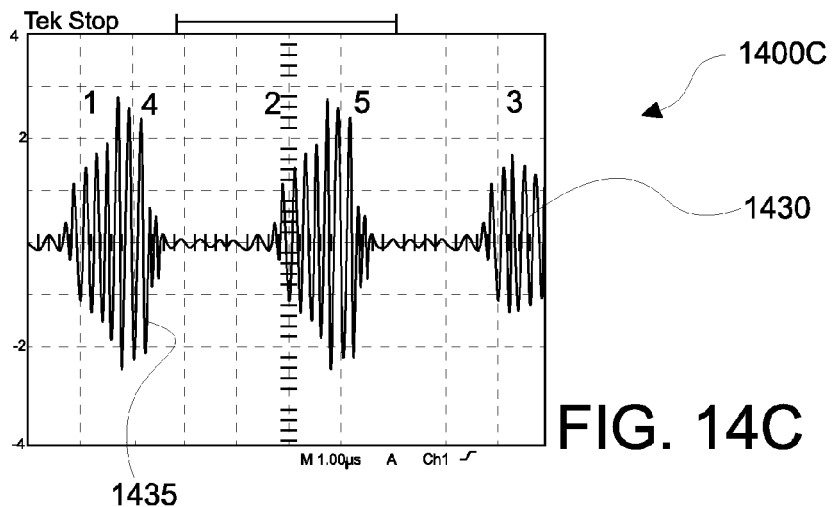

Referring to FIGS. 14A-14C, waveforms illustrating partial or incomplete destructive interference are presented. FIG. 14A shows the first channel 1400A illustrating a wave 1410, whereas FIG. 14B shows the second channel 1400B illustrating a wave 1420. The wave 1410 represents a first energy delivered to a first target tissue via a first generator 210 (see FIG. 5). The wave 1420 represents a second energy delivered to a second target tissue via a second generator 220 (see FIG. 5). FIG. 14C illustrates a waveform resulting from the addition 1400C of waveforms 1410, 1420 having different energy modes. As shown, the first waveform 1410 has an amplitude of 2V and the second waveform 1420 has an amplitude of 2V. However, the resulting waveform 1430 does not have an amplitude of 4V at every crest or peak. In other words, when both surgical instruments 530, 540 (see FIG. 5) are simultaneously used on a patient 520 and the waveforms 1410, 1420 are out-of-phase (or out of sync), the energy at some of the frequencies is additive, whereas the energy at some of the frequencies is subtractive, thus resulting in partial destructive interference.

For example, waveform 1410 includes three SINE wave portions 1, 2, 3, whereas waveform 1420 includes two SINE wave portions 4, 5. The SINE wave portions 1, 2, 3 are out-of-phase (or out of sync) with respect to the two SINE wave portions 4, 5. Therefore, in FIG. 14C, when waveforms 1410, 1420 are added, there is no constructive interference and the peaks or crests of all the SINE wave portions 1-5 are maintained within a band or region that is less than 4V.

Figure 14D:
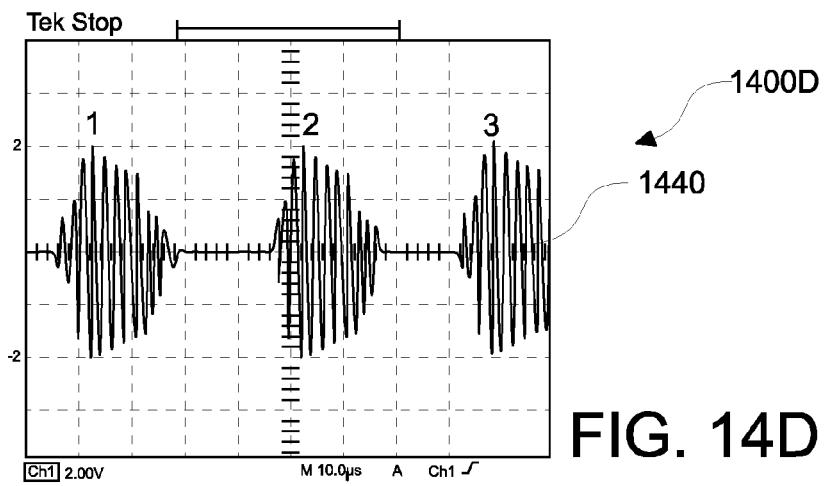
FIGS. 14D-14F are waveforms illustrating no constructive interference according to one aspect of the present disclosure.
Figure 14E:
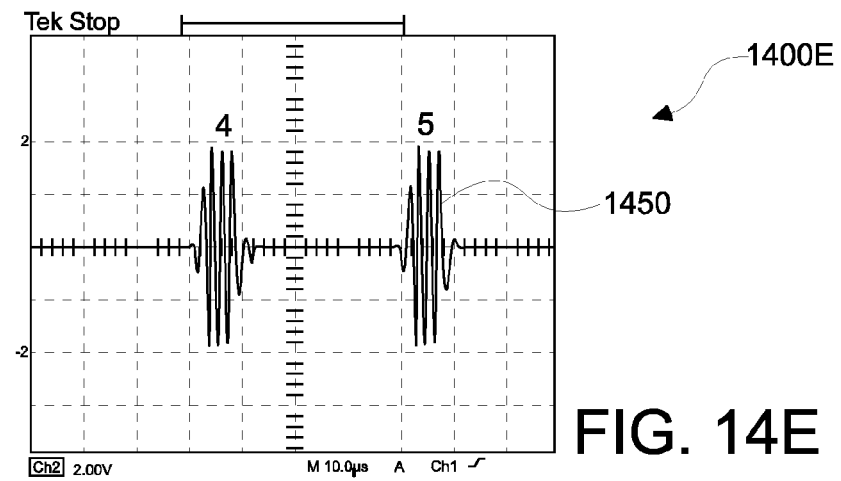
Figure 14F:
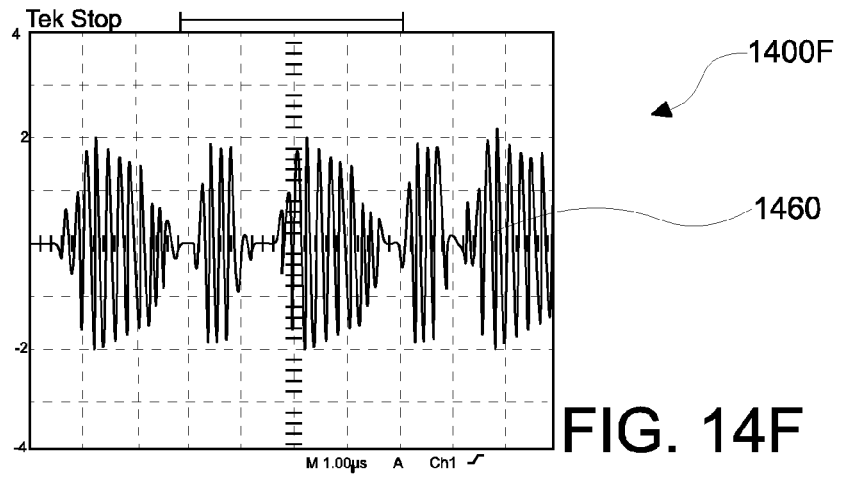

FIGS. 14D-14F are waveforms illustrating no constructive interference, according to one aspect of the present disclosure.

FIG. 14D shows a first channel 1400D illustrating a first waveform 1440, whereas FIG. 14E shows a second channel 1400E illustrating a second waveform 1450 that is out-of-phase with the first waveform 1440 by 180°. FIG. 14F illustrates a waveform resulting from the addition 1400F of first and second waveforms 1440, 1450. Waveform 1460 illustrates no constructive interference that results from the additions of waveforms 1440, 1450. As a result, waveform 1460 has an amplitude of 0° and extends along the x-axis. In other words, when both surgical instruments 530, 540 (see FIG. 5) are simultaneously used on a patient 520 and the waveforms 1440, 1450 are out-of-phase by 180°, the energy at all of the frequencies is subtractive, and the energy at all frequencies results in no constructive interference.

One objective of the partial or complete destructive interference is to lower the E field or the H field or the EM field to the surgeon or patient or support staff near the surgical site. Additionally, all the waveforms illustrated in FIGS. 14A-14F may be representative of voltage (V) or current (I) or radiated RF (V/m, A/m or power density, such as $mW/cm^2$).

Therefore, with respect to FIGS. 7A-14F, based on how the software program is executed, constructive interference may be reduced or completely eliminated when two surgical instruments 530, 540 (e.g., micro-catheters) are simultaneously used on different regions or target sites of a patient 520. Of course, one skilled in the art may contemplate using any type of surgical instruments. The term "micro-catheters" is merely used as an exemplary illustration for the reader. Thus, the term "surgical instruments" is not limited thereto.

Ideally, the two waveforms would be 180° degrees out-of-phase to completely eliminate constructive interference effects (see FIGS. 8D-8F, 10D-10F, 12D-12F, and 14D-14F). The software program would command the relative phase between the two waveforms to be adjusted, continuously and in real-time, in a number of sub-periods to provide for emissive energy reduction at certain frequencies. As a result, reduced radiation exposures for surgeons, clinicians, and patients may be achieved, as well as reduction in interference to other medical devices or equipment in the vicinity of the surgical site. Thus, the human exposure issue is being addressed herein with respect to the exemplary embodiments of the present disclosure.

It is also contemplated that the energy emission of each surgical instrument may be continuously computed and displayed on a display screen, either in the operating room or remotely. Additionally, it is contemplated that the combined energy emission may also be displayed on a display screen concurrently with the energy emission of each waveform in order to determine by how much the energy emission has been reduced. Thus, the actual energy reduction may be provided and displayed in real-time.

Figure 15A:
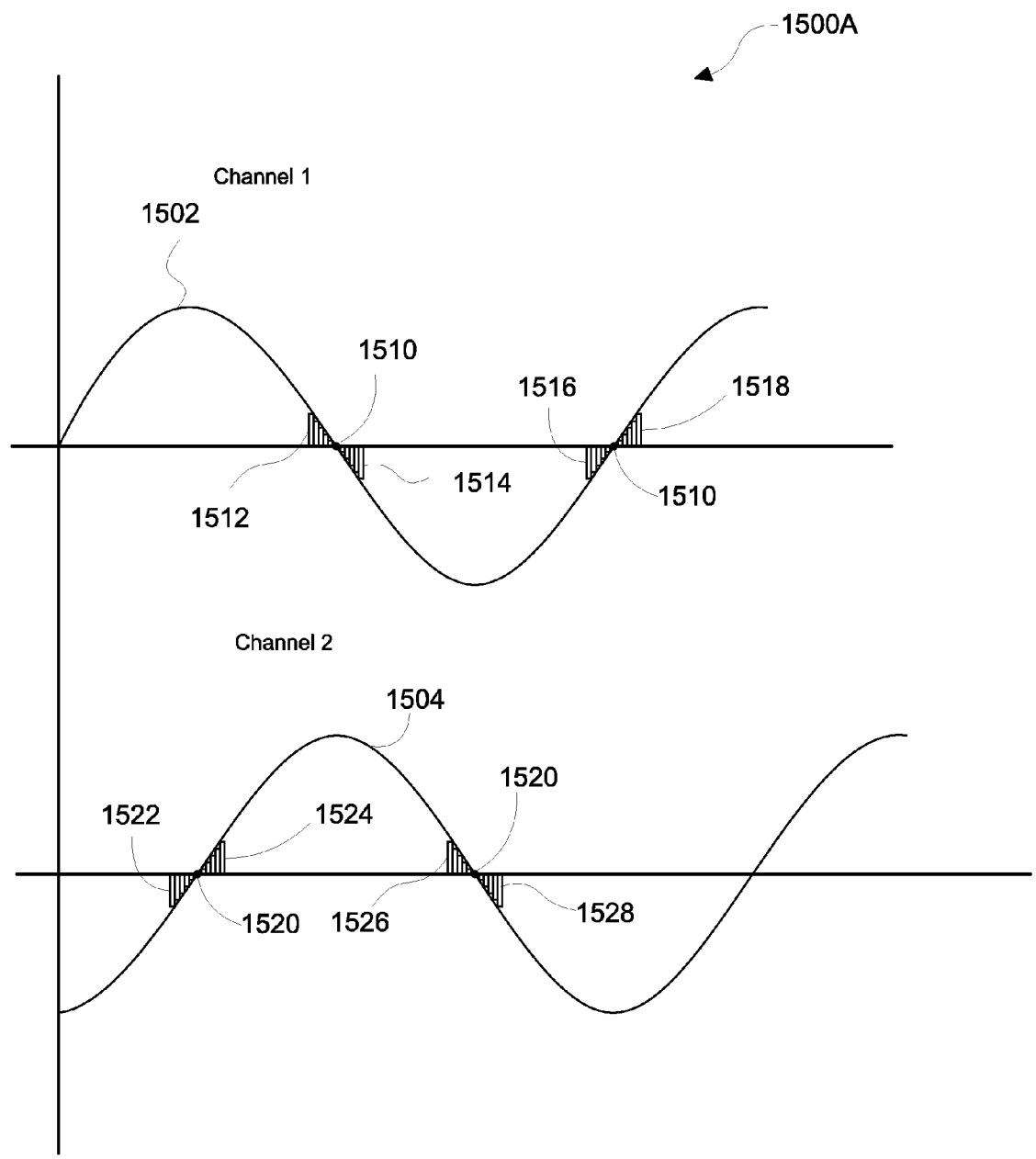
FIG. 15A is a graphical representation illustrating sampling used to determine a relative phase between two waveforms that are out-of-phase by less than 180°, according to one aspect of the present disclosure.

Referring to FIG. 15A, an illustration of sampling 1500A two waveforms 1502, 1504 are shown broken into a small number of samples that are used to determine the phase shift to achieve suitable destructive interference effects. For example, a first waveform 1502 of a first channel has two zero crossings 1510. Sampling may occur directly before and directly after the zero crossing 1510. Samples 1512, 1514, 1516, 1518 may be extracted from the first waveform 1502. Similarly, a second waveform 1504 of a second channel has two zero crossings 1520. Sampling may occur directly before and directly after the zero crossing 1520. Samples 1522, 1524, 1526, 1528 may be extracted from the second waveform 1504. The samples of the first and second waveforms 1502, 1504 near the zero crossings 1510, 1520 are analyzed and a relationship is developed therebetween. This sampling data is provided to a software algorithm for determining the relative phase between the waveforms 1502, 1504. Of course, this is merely an exemplary illustration of sampling that can be applied to any types of waveforms created by the generators 210, 220 (see FIG. 5).

Figure 15B:
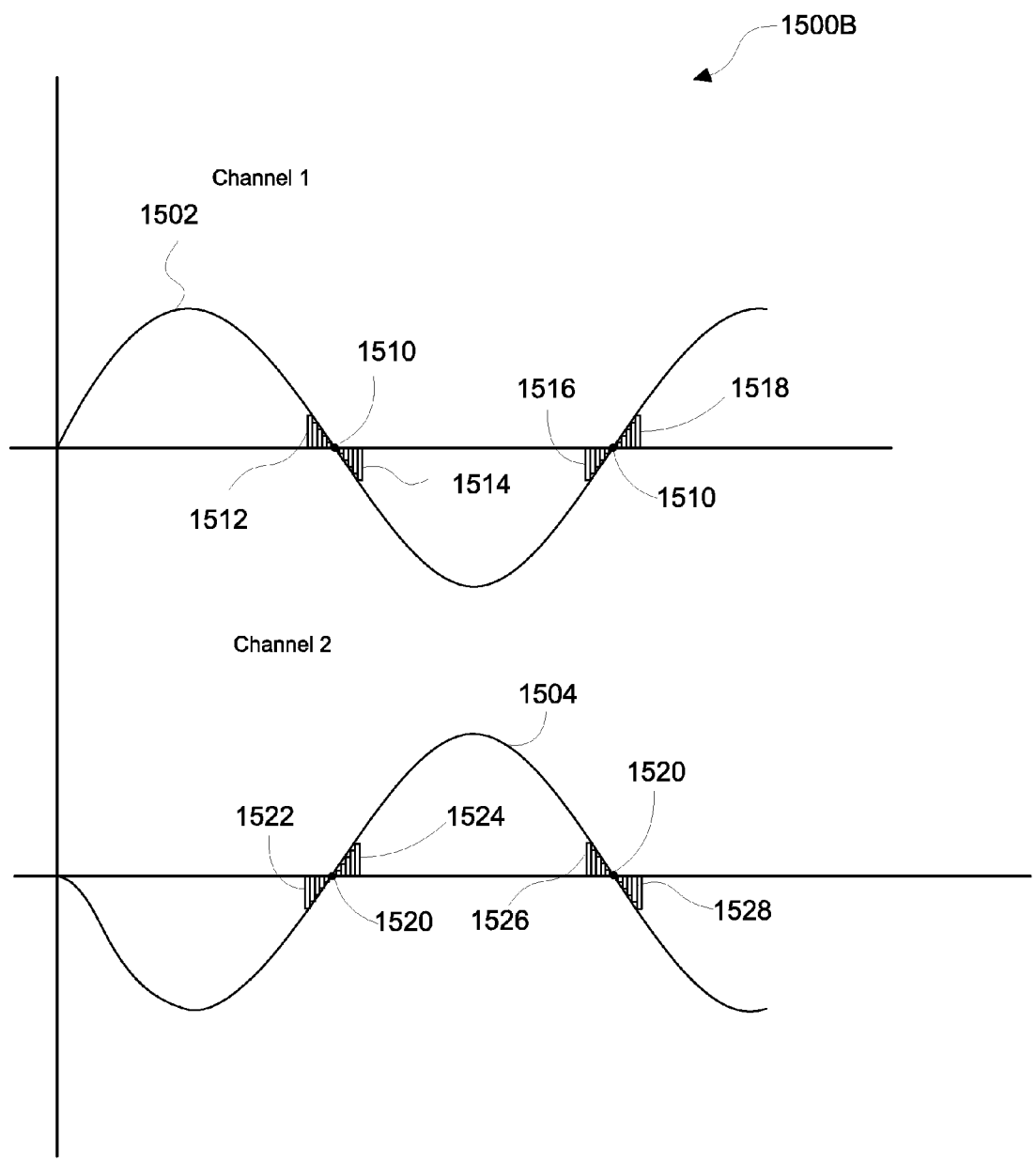
FIG. 15B is a graphical representation illustrating sampling used to determine a relative phase between two waveforms that are out-of-phase by 180°, according to one aspect of the present disclosure.

Similar to FIG. 15A, FIG. 15B is an illustration of sampling 1500B two waveforms 1502, 1504 that are shown broken into a small number of samples that are used to determine the phase shift to achieve suitable destructive interference effects. In FIG. 15B, however, the waveforms 1502, 1504 are shown to be 180° out-of-phase with respect to each other, as opposed to FIG. 15A, where the waveforms 1502, 1504 are shown to be less than 180° out-of-phase with respect to each other.

One skilled in the art may extract samples from any portion of the waveforms (i.e., not necessarily near the zero crossings) in order to provide sampling data to the software algorithm. Thus, the sampling data is used to determine the relative phase between the waveforms in order to maintain the amplitude of the waveforms within a suitable or acceptable range. Moreover, sampling may occur at a very high rate, for example, at over 20 million times per second. One skilled in the art may use any suitable sampling rate. The sampling may also occur within the generators 210, 220 or energy modules (see FIG. 5).

The illustrated devices or methods described above may be implemented in software, hardware, firmware or combinations thereof. The steps discussed herein need not be performed in the stated order. Several of the steps could be performed concurrently with each other. Furthermore, if desired, one or more of the above described steps may be optional or may be combined without departing from the scope of the present disclosure. Thus, the features and aspects of the present disclosure may be implemented in any suitable fashion by using any suitable software, firmware, and/or hardware.

For instance, when implemented via executable instructions, various elements of the present disclosure are in essence the code defining the operations of such various elements. The executable instructions or code may be obtained from a readable medium (e.g., a hard drive media, optical media, EPROM, EEPROM, tape media, cartridge media, flash memory, ROM, memory stick, and/or the like) or communicated via a data signal from a communication medium (e.g., the Internet). In fact, readable media may include any medium that may store or transfer information.

The computer means or computing means or processing means may be operatively associated with the assembly, and is directed by software to compare the first output signal with a first control image and the second output signal with a second control image. The software further directs the computer to produce diagnostic output. Further, a means for transmitting the diagnostic output to an operator of the verification device is included. Thus, many applications of the present disclosure could be formulated. The exemplary network disclosed herein may include any system for exchanging data or transacting business, such as the Internet, an intranet, an extranet, WAN (wide area network), LAN (local area network), satellite communications, and/or the like. It is noted that the network may be implemented as other types of networks.

Additionally, "code" as used herein, or "program" as used herein, may be any plurality of binary values or any executable, interpreted or compiled code which may be used by a computer or execution device to perform a task. This code or program may be written in any one of several known computer languages. A "computer," as used herein, may mean any device which stores, processes, routes, manipulates, or performs like operation on data. A "computer" may be incorporated within one or more transponder recognition and collection systems or servers to operate one or more processors to run the transponder recognition algorithms. Moreover, computer-executable instructions include, for example, instructions and data which cause a general purpose computer, special purpose computer, or special purpose processing device to perform a certain function or group of functions. Computer-executable instructions also include program modules that may be executed by computers in stand-alone or network environments. Generally, program modules include routines, programs, objects, components, and data structures, etc. that perform particular tasks or implement particular abstract data types.

It is noted that the energy modes are at least one of bipolar, monopolar, continuous, and discontinuous modes. It is further noted that the modality is selected from the group consisting of cutting, coagulation, blend, division with hemostasis, fulguration, spray, and combinations thereof. Of course, one skilled in the art may contemplate a number of other energy modes and/or modalities based on different desired applications.

Reference throughout this specification to "one embodiment," "an embodiment," or similar language means that a particular feature, structure, or characteristic described in connection with the embodiment is included in at least one embodiment of the present disclosure. Thus, appearances of the phrases "one embodiment," "an embodiment," and similar language throughout this specification may, but do not necessarily, all refer to the same embodiment, different embodiments, or component parts of the same or different illustrated disclosure. Additionally, reference to the wording "an embodiment," or the like, for two or more features, elements, etc. does not mean that the features are related, dissimilar, the same, etc. The use of the term "an embodiment," or similar wording, is merely a convenient phrase to indicate optional features, which may or may not be part of the present disclosure as claimed. The independent embodiments are considered to be able to be combined in whole or in part one with another as the claims and/or art may direct, either directly or indirectly, implicitly or explicitly.

Moreover, the fact that the wording "an embodiment," or the like, does not appear at the beginning of every sentence in the specification, such as is the practice of some practitioners, is merely a convenience for the reader's clarity. However, it is the intention of this application to incorporate by reference the phrasing "an embodiment," and the like, at the beginning of every sentence herein where logically possible and appropriate.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A modular electrosurgical generator platform, comprising:
    a power supply module configured to output power;
    a first energy module configured to receive the power and convert the power into a first waveform having a first phase, and to deliver the power in a first energy mode;
    a second energy module configured to receive the power and convert the power into a second waveform having a second phase, and to deliver the power in a second energy mode;
    a host controller module configured to control a type and a number of energy modalities provided by the generator platform;
    a comparator for comparing the first phase of the first waveform with the second phase of the second waveform in two or more of a plurality of sub-periods, the comparator for identifying a combined waveform of the first waveform and the second waveform having a lowest constructive interference among a plurality of phase differentials between the first and second waveforms, the phase differentials being associated with respective sub-periods; and an adjustment module for adjusting a relative phase between the first and second generators based on results obtained from the comparator, the adjustment module offsetting the first phase from the second phase by a predetermined amount, the predetermined amount being an integer multiple of sub-periods, the offsetting resulting in destructive interference of the first and second energy waveforms wherein constructive interference is less than a predetermined maximum value, the integer multiple of sub-periods being associated with the lowest constructive interference.

2. The modular electrosurgical generator platform according to claim 1, wherein the energy modality is selected from the group consisting of cutting, coagulation, blend, division with hemostasis, fulguration, spray, and combinations thereof.

3. The modular electrosurgical generator platform according to claim 1, wherein the first and second energy modules includes an RF stage, a sensor stage, a controller stage, and a connector module stage.

4. The modular electrosurgical generator platform according to claim 3, wherein the RF stage includes an inverter and a preamp.

5. The modular electrosurgical generator platform according to claim 1, wherein the generator platform supports simultaneous activation of two energy modes.

6. The modular electrosurgical generator platform according to claim 5, wherein the host controller module manages requests and controls activation of energy modes.

7. The modular electrosurgical generator platform according to claim 1, wherein the relative phase is adjusted at predefined frequencies.

8. The modular electrosurgical generator platform according to claim 1, wherein the first waveform is applied in a first energy mode and the second waveform is applied in a second energy mode.

9. The modular electrosurgical generator platform according to claim 8, wherein the first energy mode is a cutting mode and the second energy mode is a coagulation mode.

10. The modular electrosurgical generator platform according to claim 8, wherein the first energy mode is a coagulation mode and the second energy mode is a blend mode.

11. The modular electrosurgical generator platform according to claim 8, wherein the first energy mode is a blend mode and the second energy mode is a division with hemostasis mode.

12. The modular electrosurgical generator platform according to claim 8, wherein the first energy mode is a division with hemostasis mode and the second energy mode is a fulguration mode.

13. The modular electrosurgical generator platform according to claim 1, wherein:

the host controller module is configured to control a plurality of energy modalities, at least two of the energy modalities being of a different type.

* * * * *